(12) United States Patent
Pizza

(10) Patent No.: US 8,663,656 B2
(45) Date of Patent: Mar. 4, 2014

(54) POLYPEPTIDE-VACCINES FOR BROAD PROTECTION AGAINST HYPERVIRULENT MENINGOCOCCAL LINEAGES

(75) Inventor: Mariagrazia Pizza, Siena (IT)

(73) Assignee: Novartis AG, Basel (CH)

( * ) Notice: Subject to any disclaimer, the term of this patent is extended or adjusted under 35 U.S.C. 154(b) by 614 days.

(21) Appl. No.: 10/530,753

(22) PCT Filed: Oct. 2, 2003

(86) PCT No.: PCT/IB03/04848
§ 371 (c)(1),
(2), (4) Date: Mar. 3, 2006

(87) PCT Pub. No.: WO2004/032958
PCT Pub. Date: Apr. 22, 2004

(65) Prior Publication Data
US 2006/0171957 A1    Aug. 3, 2006

(30) Foreign Application Priority Data

Oct. 11, 2002  (GB) .................. 0223741.0
Mar. 13, 2003  (GB) .................. 0305831.0
Apr. 22, 2003  (GB) .................. 0309115.4

(51) Int. Cl.
*A61K 39/095* (2006.01)

(52) U.S. Cl.
USPC .................................................. 424/249.1

(58) Field of Classification Search
None
See application file for complete search history.

(56) References Cited

U.S. PATENT DOCUMENTS

| | | | |
|---|---|---|---|
| 4,239,746 A | 12/1980 | Bartos et al. | |
| 4,239,749 A | 12/1980 | Buchanan | |
| 5,268,270 A | 12/1993 | Meyer et al. | |
| 5,286,484 A | 2/1994 | Rodriquez et al. | |
| 5,547,670 A | 8/1996 | Goldstein et al. | |
| 6,013,267 A | 1/2000 | Blake et al. | |
| 6,028,049 A | 2/2000 | Jacobs et al. | |
| 6,197,312 B1 | 3/2001 | Peak et al. | |
| 6,248,329 B1 | 6/2001 | Chandrashekar et al. | |
| 6,476,201 B1 | 11/2002 | Lowell et al. | |
| 6,709,660 B1 | 3/2004 | Scarlato et al. | |
| 6,914,131 B1 | 7/2005 | Scarlato et al. | |
| 7,238,345 B1 | 7/2007 | Seid et al. | |
| 7,348,006 B2 | 3/2008 | Contorni et al. | |
| 7,368,261 B1 | 5/2008 | Rappuoli | |
| 7,504,111 B2 | 3/2009 | Fontana et al. | |
| 7,576,176 B1 | 8/2009 | Fraser et al. | |
| 7,604,810 B2 | 10/2009 | Rappuoli | |
| 7,612,192 B2 | 11/2009 | Fraser et al. | |
| 7,655,245 B2 | 2/2010 | Scarlato et al. | |
| 7,662,588 B2 | 2/2010 | Judd et al. | |
| 7,700,119 B2 | 4/2010 | Giuliani et al. | |
| 7,714,121 B2 | 5/2010 | Scarlato et al. | |
| 7,749,518 B2 | 7/2010 | Masignani et al. | |
| 7,838,015 B2 | 11/2010 | O'Hagan et al. | |
| 7,862,827 B2 | 1/2011 | Giuliani et al. | |
| 7,928,192 B2 | 4/2011 | Masignani et al. | |
| 8,273,360 B2 | 9/2012 | Pizza et al. | |
| 2002/0146764 A1 | 10/2002 | Cousens et al. | |
| 2002/0160016 A1 | 10/2002 | Peak et al. | |
| 2003/0215469 A1 | 11/2003 | Robinson et al. | |
| 2004/0092711 A1 | 5/2004 | Arico et al. | |
| 2004/0101537 A1* | 5/2004 | O'Hagan et al. | 424/249.1 |
| 2004/0110670 A1 | 6/2004 | Arico et al. | |
| 2004/0167068 A1 | 8/2004 | Zlotnick et al. | |
| 2005/0222385 A1 | 10/2005 | Pizza | |
| 2005/0232936 A1 | 10/2005 | Arico et al. | |
| 2006/0051840 A1 | 3/2006 | Arico et al. | |
| 2006/0171957 A1 | 8/2006 | Pizza | |
| 2006/0240045 A1 | 10/2006 | Berthet et al. | |
| 2006/0251670 A1 | 11/2006 | Comanducci et al. | |
| 2007/0026021 A1 | 2/2007 | Fraser et al. | |
| 2007/0053926 A1 | 3/2007 | Masignani et al. | |
| 2007/0082014 A1 | 4/2007 | Costantino | |
| 2007/0219347 A1 | 9/2007 | Fraser et al. | |
| 2008/0124353 A1 | 5/2008 | Brodeur et al. | |
| 2008/0166370 A1 | 7/2008 | Serino et al. | |
| 2008/0193971 A1 | 8/2008 | Serruto et al. | |
| 2008/0241180 A1 | 10/2008 | Contorni | |
| 2009/0182129 A1 | 7/2009 | Costantino | |

(Continued)

FOREIGN PATENT DOCUMENTS

| EP | 0273116 | 7/1988 |
|---|---|---|
| EP | 0467714 | 1/1992 |

(Continued)

OTHER PUBLICATIONS

Bowie et al. (Science, 1990, 247:1306-1310).*

(Continued)

*Primary Examiner* — Brian J Gangle

(74) *Attorney, Agent, or Firm* — Amy Hessler; Otis Littlefield

(57) ABSTRACT

A small number of defined antigens can provide broad protection against meningococcal infection, and the invention provides a composition which, after administration to a subject, is able to induce an antibody response in that subject, wherein the antibody response is bactericidal against two or three of hypervirulent lineages A4, ET 5 and lineage 3 of *N. meningitidis* serogroup B. Rather than consisting of a single antigen, the composition comprises a mixture of 10 or fewer purified antigens, and should not include complex or undefined mixtures of antigens such as outer membrane vesicles. Five protein antigens are used in particular: (1) a 'NadA' protein; (2) a '741' protein; (3) a '936' protein; (4) a '953' protein; and (5) a '287' protein.

10 Claims, No Drawings

(56) References Cited

U.S. PATENT DOCUMENTS

| | | |
|---|---|---|
| 2009/0232820 A1 | 9/2009 | Fraser et al. |
| 2009/0285845 A1 | 11/2009 | Masignani et al. |
| 2010/0015151 A1 | 1/2010 | Rappuoli et al. |
| 2010/0092509 A1 | 4/2010 | Costantino et al. |
| 2010/0143418 A1 | 6/2010 | Contorni et al. |
| 2010/0267931 A1 | 10/2010 | Arico et al. |
| 2011/0033500 A1 | 2/2011 | Biemans et al. |

FOREIGN PATENT DOCUMENTS

| | | |
|---|---|---|
| EP | 0624376 | 11/1994 |
| EP | 0978565 | 2/2000 |
| EP | 1790660 | 5/2007 |
| FR | 2720408 | 12/1995 |
| NL | 8901612 | 7/1990 |
| WO | WO-90/06696 | 6/1990 |
| WO | WO-9006696 | 6/1990 |
| WO | WO-9216643 | 10/1992 |
| WO | WO-94/08021 | 4/1994 |
| WO | WO-9503413 | 2/1995 |
| WO | WO-9533049 | 12/1995 |
| WO | WO-9629412 | 9/1996 |
| WO | WO-9710844 | 3/1997 |
| WO | WO-9713860 | 4/1997 |
| WO | WO-9728273 | 8/1997 |
| WO | WO-98/02547 | 1/1998 |
| WO | WO 9817805 | 4/1998 |
| WO | WO-9924578 | 5/1999 |
| WO | WO-99/31132 | 6/1999 |
| WO | WO-9936544 | 7/1999 |
| WO | WO-99/55873 | 11/1999 |
| WO | WO-99/58683 | 11/1999 |
| WO | WO 9957280 A2 * | 11/1999 |
| WO | WO-00/11182 | 3/2000 |
| WO | WO-00/23595 | 4/2000 |
| WO | WO-0022430 | 4/2000 |
| WO | WO-00/25811 A2 | 5/2000 |
| WO | WO-0050075 | 8/2000 |
| WO | WO-00/66741 A2 | 11/2000 |
| WO | WO-0066791 | 11/2000 |
| WO | WO-0071574 | 11/2000 |
| WO | WO-0071725 | 11/2000 |
| WO | WO-01/09350 A2 | 2/2001 |
| WO | WO-0131019 | 5/2001 |
| WO | WO-0152885 | 7/2001 |
| WO | WO-01/55182 | 8/2001 |
| WO | WO 01 64920 A | 9/2001 |
| WO | WO 01 64922 A | 9/2001 |
| WO | WO-0164922 | 9/2001 |
| WO | WO-01/072337 | 10/2001 |
| WO | WO-03/009869 A1 | 2/2003 |
| WO | WO 03 010194 A | 2/2003 |
| WO | WO 03 020756 A | 3/2003 |
| WO | WO-03/063766 | 8/2003 |
| WO | WO-2004/014417 | 2/2004 |
| WO | WO-2004032958 | 4/2004 |
| WO | WO-2004048404 | 6/2004 |
| WO | WO-2004067030 | 8/2004 |
| WO | WO-2004112832 | 12/2004 |
| WO | WO-2005032583 | 4/2005 |
| WO | WO-2005033148 | 4/2005 |
| WO | WO-2005102384 | 11/2005 |
| WO | WO-2005106009 | 11/2005 |
| WO | WO 2006024954 | 3/2006 |
| WO | WO-2006/081259 | 8/2006 |
| WO | WO-2007/060548 A2 | 5/2007 |
| WO | WO-2008001224 | 1/2008 |
| WO | WO-2009/104097 A2 | 8/2009 |
| WO | WO-2010/046715 A1 | 4/2010 |

OTHER PUBLICATIONS

Greenspan et al. (Nature Biotechnology, 7:936-937, 1999).*
Cruse et al., Illustrated Dict. of Immunology, 2nd ed., CRC Press, 2003, pp. 46, 166, 382.*
McGuinness et al. (Mol. Microbiol., 7:505-514, 1993).*
Moudallal et al. (EMBO Journal, 1:1005-1010, 1982).*
Silk, Excerpt from On the Shores of the Unknown, A Short History of the Universe, Cambridge University Press.*
Blythe et al. (Protein Sci., 14:246-248, 2005).*
Comanducci Maurizio et al: "NadA, a novel vaccine candidate of *Neisseria meningitides*", Journal of Experimental Medicine, vol. 195, No. 11, Jun. 3, 2002, pp. 1445-1454, XP002272871.
Grifantini Renata et al: "Previously unrecognized vaccine candidates against group B meningococcus identified by DNA microarrays", Nature Biotechnology, vol. 20, No. 9, Sep. 2002, pp. 914-921, XP002272872.
Abad et al. (2008). "PorB2/3 Protein Hybrid in *Neisseria meningitidis*," Emerging Infectious Diseases, 14(4):688-689.
Ala'Aldeen et al. (1996). "The Meningococcal Transferrin-binding Proteins 1 and 2 are Both Surface Exposed and Generate Bactericidal Antibodies Capable of Killing Homologous and Heterologous Strains," Vaccine 14(1):49-53.
Bartsevich et al. (Mar. 7, 1997). "Molecular Identification of a Novel Protein That Regulates Biogenesis of Photosystem I, a Membrane Protein Complex," the Journal of Biological Chemistry 272(10):6382-6387.
Bethell et al. (2002). "Meningococcal vaccines," Expert Review of Vaccines 1(1):75-84.
Boslego et al. (1991). "Gonorrhea Vaccines" Chapter 17 in Vaccines and Immunotherapy, S. Cryz (Ed.). pp. 211-223.
Bygraves et al. (1992). "Analysis of the Clonal Relationships Between Strains of *Neisseria meningitidis* by Pulsed Field Gel Electrophoresis," Journal of General Microbiology 138:523-531.
Cann et al. (1989). "Detection of Antibodies to Common Antigens of Pathogenic and Commensal *Neisseria* Species," Journal of Medical Microbiology 30:23-30.
Caugant et al. (1987). "Genetic Structure of *Neisseria meningitidis* Populations in Relation to Serogroup, Serotype, and Outer Membrane Protein Pattern," Journal of Bacteriology 169(6):2781-2792.
Christodoulides et al. (1994). "Immunization with a Multiple Antigen Peptide Containing Defined B- and T-Cell Epitopes: Production of Bacterial Antibodies Group B *Neisseria meningitidis*," Microbiology 140:2951-2960.
Cooney et al. (1993). "Three Contiguous Lipoprotein Genes in *Pasteurella haemolytica* A1 which are Homologous to a Lipoprotein Gene in Haemophilus Influenza Type B," Infection and Immunity 61 (11):4682-4688.
Dempsey et al. (1991). "Physical Map of the Chromosome of *Neisseria gonorrhoeae* FA1090 with Locations of Genetic Markers, including Opa and Pil Genes," Journal of Bacteriology 173(17):5476-5486.
Devries et al. (Aug. 1996). "Invasion of Primary Nasopharyngeal Epithelial Cells by *Neisseria meningitidis* is Controlled by Phase Variation of Multiple Surface Antigens," Infection and Immunity 64(8):2998-3006.
Ellis (1988). "New Technologies for Making Vaccines" in Vaccines. Plotkin et al. (Eds.) pp. 568-575.
Feng et al. (1996). "P55, an Immunogenic but Nonprotective 55-Kilodalton *Borrelia burgdorferi* Protein in Murine Lyme Disease," Infection and Immunity. 64(1):363-365.
Gervais et al. (1992). "Putative Lipoprotein Yaec Precursor," Database Swissport Acc No. p28635.
Guillen et al. (1996). "Expression in *Escherichia coli* and Immunological Characterization of a Hybrid Class I-P64K Protein from *Neisseria meningitidis*," Biotecnologia Aplicada13(4):271-275.
Herbert et al. (1995). The Dictionary of Immunology. Academic Press: London 4th edition, 3 pages.
Herbert et al. (1985). The Dictionary of Immunology. Academic Press: London 3rd edition, pp. 58-59.
Holmes, E. (2001). "PSMA Specific Antibodies and their Diagnostic and Therapeutic Use," Expert Opinion on Investigational Drugs 10(3): 511-519.
Jacobsson et al. (2009). Vaccine. 27:1579-1584.
Jolley et al. (2007). "Molecular typing of meningococci: recommendations for target choice and nomenclature," FEMS Microbiol. Rev. 31:89-96.

(56) References Cited

OTHER PUBLICATIONS

Legrain et al. (1995). "Production of Lipidated Meningococcal Transferrin Binding Protein 2 in *Escherichia coli*," Protein Expression and Purification 6:570-578.
Maiden et al. (1998). "Multilocus Sequence Typing: a Portable Approach to the Identification of Clones within Populations of Pathogenic Microorganisms," Proceedings of the National Academy of Sciences USA 95:3140-3145.
Morley et al. (2002). "Vaccine prevention of meningococcal disease, coming soon?" Vaccine 20:666-687.
Ni et al. (1992). "Phylogenetic and Epidemiological Analysis of *Neisseria meningitidis* Using DNA Probes," Epidemiology and Infection 109:227-239.
Perkins et al. (1998). "Immunogenicity of two efficacious outer membrane protein-based serogroup B meningococcal vaccines among young adults in Iceland," The Journal of Infectious Disease 177:683-691.
Perrett et al. (2005). "Towards an improved serogroup B *Neisseria meningitidis* vaccine," Expert Opinion on Biological Therapy 5(12):1611-1625.
Pettersson et al. (1999). "Sequence Variability of the Meningococcal Lactoferrin-binding Protein LbpB," Gene 231:105-110.
Pizza et al. (Mar. 10, 2000). "Identification of Vaccine Candidates Against Serogroup B Meningococcus by Whole-Genome Sequencing," Science 287(5459):1816-1820.
Poolman et al. (1985). "Colony Variants of *Neisseria meningitidis* Strain 2996 (B:2b:P1.2): Influence of Class-5 Out Membrane Proteins and Lipopolysaccharides," J. Med. Microbiol 19:203-209.
Poolman et al. (1988). "Outer membrane protein serosubtyping of *Neisseria meningitidis*," European Journal of Clinical Microbiology and Infectious Diseases 7(2):291-292.
Poolman (1995). "Development of a Meningococcal Vaccine," Infectious Agents and Disease 4:13-28.
Renauld-Mongenie et al. (1997). "Identification of Human Transferrin-Binding Sites Within Meningococcal Transferrin-Binding Protein B," J. Bacteriology 197(20):6400-6407.
Roitt, I. et al. (1993). Immunology. Mosby: St. Louis, 4$^{th}$ edition, pp. 7,7-7,8.
Rosenqvist et al. (1995). "Human Antibody Response to Meningococcal Outer Membrane Antigens after Three Doses of the Norwegian Group B Meningococcal Vaccine," Infection and Immunity 63(12):4642-4652.
Seiler et al. (1996). "Allelic polymorphism and site-specific recombination in the opc locus of *Neisseria meningitidis*," Molecular Microbiology 19(4):841-856.
Telford (Jun. 2008). "Bacterial Genome Variability and Its Impact on Vaccine Design," Cell Host & Microbe 3(6):408-416.
Tettelin et al. (2006). "Towards a universal group B Streptococcus vaccine using multistrain genome analysis," Expert Rev Vaccines 25:687-694.
Tettelin et al. (Mar. 10, 2000). "Complete Genome Sequence of *Neisseria meningitidis* Serogroup B Strain MC58," Science 287(5459):1809-1815.
Thompson et al. (1994). "Clustal W: Improving the Sensitivity of Progressive Multiple Sequence Alignment through Sequence Weighting, Position-specific Gap Penalties and Weight Matrix Choice," Nucleic Acids Research 22(22):4673-4680.
Thompson et al. (1998). "Multiple Sequence Alignment with Clustal X," Trends in Biochemical Sciences 23:403-405.
Van Der Lay et al. (1992). "Construction of a Multivalent Meningococcal Vaccine Strain Based on the Class I Outer Membrane Protein," Infection and Immunity 60(8): 3516-3161.
Van Der Lay et al. (1995). "Construction of Neisseria Meningitidis Strains Carrying Multiple Chromosomal Copies of the PorA Gene for Use in Production of a Multivalent Outer Membrane Vesicle Vaccine," Vaccine 13(4): 401-107.
Virji et al. (1992). "Variations in the Expression of Pili: the Effect on Adherence of *Neisseria meningitidis* to Human Epithelial and Endothelial Cells," Molecular Microbiology 6:1271-1279.

Wolff et al. (1992). "Phylogeny and Nucleotide Sequence of a 23S rRNA Gene from *Neisseria gonorrhea* and *Neisseria meningitidis*," Nucleic Acids Research 20(17):4657.
Database accession No. NMB1994.Tettelin at al. (Mar. 2, 2010).
Bowe at al. (Jul. 2004) "Mucosal vaccination against serogroup B meingococci: induction of bacterial antibodies and cellular immunity following intranasal immunization with NadA of *Neisseria meningitides* and mutants of *Escherichia coli* heat-labile enterotoxin," Infection and Immunity, 72: 4052-4060.
Capecchi at al. (2005) "*Neisseria meningitides* NadA is a new invasion which promotes bacterial adhesion to and penetration into human epithelial cells," Molecular Microbiology, 55: 687-698.
Comanducci at al. (Jul. 2004) "NadA diversity and carriage in *Neisseria meningitides*," Infection and Immunity, 72: 4217-4223.
Koeberling at al. (2007). "Improved immunogenicity of a H44/76 group B outer membrane vesicle vaccine with over-expressed genome-derived," Neisserial antigen 1870. Vaccine 25:1912-1920.
Martin et al. (2005) "Experimentally revised repertoire of putative contingency loci in *Neisseria meningitides* strain MC58: evidence for a novel mechanism of phase variation" 50: 245-257.
Parkhill et al. (Mar. 2000) "Complete DNA sequence of a serogroup A strain of *Neisseria meningitides* Z2491" 404: 502-505.
Stabler et al. (2005) "Identification of pathogen-specific genes through microarray analysis of pathogenic and commensal *Neisseria* species" vol. 151, pp. 2907-2922.
Turner et al. (2006). "Characterization of MspA, an Immunogenic Autotransporter Protein That Mediates Adhesion of Epithelial and Endothelial Cells in *Neisseria meningitidis*," Infection and Immunity 74(5):2957-2964.
United States Office Action mailed on Feb. 11, 2009, for U.S. Appl. No. 10/181,600, filed Jan. 17, 2001, 5 pages.
United States Office Action mailed on Jul. 24, 2008, for U.S. Appl. No. 10/181,600, filed Jan. 17, 2001, 23 pages.
United States Office Action mailed on Jul. 7, 2009, for U.S. Appl. No. 10/181,600, filed Jan. 17, 2001, 23 pages.
Hou et al. (2005). "Protective Antibody Responses Elicited by a Meningococcal Outer Membrane Vesicle Vaccine with Overexpressed Genome-Derived Neisserial Antigen 1870," J Infect Dis 192(4):580-90.
Zhu et al. (2005). "Evaluation of Recombinant Lipidated P2086 Protein as a Vaccine Candidate for Group B *Neisseria meningitidis* in a Murine Nasal Challenge Model," Infect Immun 73(10):6838-45.
European Search Report and Written Opinion mailed Sep. 29, 2009, for EP Application No. 08153843 filed Jul. 31, 2003, 27 pages.
Fredrikson et al. (1991). "Production, characterization and control of MenB-vaccine 'Folkehelsa': an outer membrane vesicle vaccine against group B meningococcal disease," NIPH Annals 14:67-79.
Gao et al. (1996). "Study on the LOS Antigenicity of 2 Candidate Strains for Meningococcal Vaccine of Serogroup B," Zhonghua Weishengwuxue He Mianyixue Zazhi 16(6):405-408. (English language Abstract only).
Jennings et al., (1984). "Conjugation of Meningococcal Lipopolysaccharide R-Type Oligosaccharides to Tetanus Toxoid as Route to a Potential Vaccine Against Group B *Neisseria meningitidis*" Infection and Immunity 43(1):407-412.
Rouppe van der Voort et al. (1996). "Specificity of human bactericidal antibodies against PorA P1.7,16 induced with a hexavalent meningococcal outer membrane vesicle vaccine," Infect. Immun. 64:2745-2751.
Rune Anderson et al. (1997), "Lipopolysaccharide heterogeneity and escape mechanisms of *Neisseria meningitidis*: possible consequences for vaccine development," Microbial Pathogenesis 23:139-155.
Verheul et al., (1991). "Preparation, Characterization, and Immunogenicity of Meningococcal Immunotype L2 and L3,7,9 Phosphoethanolamine Group-Containing Oligosaccharide-Protein Conjugates," Infection and Immunity 59(3):843-851.
1997-11-17-NM_shotgun.dbs and 1997-12-15-Nm.dbs, located at, <ftp://ftp.sanger.ac.uk/pub/pathogens/nm/old data/>, 2008.
JCVI-CMR website showing Z2491 Sanger sequence (http://cmr.jcvi.org/tigr-scripts/CMR/shared/Genomes.cgi and links), 2010.
Post by Dr. Parkhill on BIOSCl/Bionet of May 8, 1998.

(56) References Cited

OTHER PUBLICATIONS

PSORT analysis of 200 of the sequences disclosed in PCT/US99/09346 (i.e., the original application underlying the Patent; published as WO99/057280), 2010.
PSORT analysis of SEQ ID Nos. 4 and 6, and of 'Contig295' 300mer, 2010.
Supplemental Submission in Opposition against European Patent EP 1645631, granted on Oct. 24, 2007. Opposition filed on May 25, 2010. 28 pages.
Cornelissen et al. (1992) "Gonococcal transferrin-binding protein 1 is required for transferrin utilization and is homologous to TonB-dependent outer membrane receptors," J Bacteriol 174(18): 5788-5797.
European Office Action dated Nov. 14, 2011 for EP Application No. 03784153, 7 pages.
Milagres L G et al. (Aug. 2000) "Bactericidal antibody response to Neisseria meningitidis serogroup B in patients with bacterial meningitis: effect of immunization with an outer membrane protein vaccine," FEMS Immunology and Medical Microbiology 28(4):319-327.
Third Party Observations dated Mar. 4, 2010 for EP Application No. 03784153, 3 pages.
Third Party Observations dated Sep. 26, 2011 for EP Application No. 03784153, 4 pages.
Response to European Office Action dated Jul. 30, 2010 for EP Application No. 03784153, 5 pages.
Vandenbergh et al. (1983). "Iron-Chelating Comppounds Produced by Soil Pseudomondas: Correlation with Fungal Growth Inhibition," Applied and Environmental Microbiology 46(1):128-132.
1997-11-17-NM_shotgun.dbs and 1997-12-15-NM.dbs, located at <ftp://ftp.sanger.ac.uk/pub/pathogens/nm/old data/>.
Aasel et al. (1998). Abstract from the 11th International Pathogenic Neisseria Conference, Nice France, Nov. 1-6, 1998. pp. 37-38.
Bernfield L. et al. (Sep. 2002). "Identification of a novel vaccine candidate for group B Neisseria meningitidis," Thirteenth International Pathogenic Neisseria Conference, Norwegian Institute of Public Health, Oslo, Norway, pp. 116.
Boslego et al. (1991). "Gonorrhea Vaccines," Chapter 17 In Vaccines and Immunotherapy, Cryz S.J. (Ed.), Pergamon Press: New York, NY, pp. 211-223.
Cannon (1989). "Conserved Lipoproteins of Pathogenic Neisseria Species Bearing the H.8 Epitope: Lipid-Modified Azurin and H.8 Outer Membrane Protein," Clinical Microbiology Reviews, vol. 2, Suppl., S1-S4.
Cantini et al. (Mar. 2006). "Solution Structure of the Immunodominant Domain of Protective Antigen GNA 1870 of Neisseria meningitidis," Journal of Biological Chemistry 281(11): 7220-7227.
Declaration by Dr. Julian Parkhill dated Jun. 12, 2008. 2 pages.
Farley J. et al. (Sep. 2002). "Characterization, cloning and expression of different subfamilies of the ORF 2086 gene from Neisseria meningitidis," Thirteenth International Pathogenic Neisseria Conference, Norwegian Institute of Public Health, Oslo, Norway, p. 124.
Feavers et al. (2009). "Meningococcal protein antigens and vaccines," Vaccine 275:B42-B50.
Fleischmann et al. (1995). "Whole-Genome Random Sequencing and Assembly of Haemophilus influenzae Rd," Science 269:496-501.
Fletcher et al. (2004). "Vaccine Potential of the Neisseria meningitidis 2086 Lipoprotein," Infection and Immunity 72(4): 2088-2100.
Fontana et al. (2002). "A genomic approach to identify vaccine candidates against gonococcus." Abstract from the 13th International Pathogenic Neisseria Conference, Oslo, Norway, Sep. 1-6, 2002. p. 248.
Giuliani et al. (2006). "A universal vaccine for serogroup B meningococcus," PNAS 103(29):10834-10839.
Giuliani et al. (Feb. 2005). "The Region Comprising Amino Acids 100 to 255 of Neisseria meningitidis Lipoprotein GNA 1870 Elicits Bactericidal Antibodies," Infection and Immunity 73(2): 1151-1160.
JCVI-CMR website showing Z2491 Sanger sequence (http://cmr.jcvi.org/tigr-scripts/CMR/shared/Genomes.cgi and links).
Masignani V. (Mar. 17. 2003). "Vaccination against Neisseria meningitidis using three variants of the lipoprotein GNA1870," J. Exp. Med. 197(6):789-799.
Morley, S. et al. (Dec. 12, 2001). "Vaccine prevention of meningococcal disease, coming soon?" Vaccine 20(5-6):666-687.
Nassif (2000). "A Furtive Pathogen Revealed," Science 287: 1767-1768.
Phase II clinical results for Novartis vaccine, Oct. 9, 2008.
Post by Dr. Parkhill on BIOSCI/Bionet of May 8, 1998.
Progress through the Sanger Institute FTP server. FTP root at ftp.sanger.ac.uk, 2010.
PSORT analysis of 200 of the sequences disclosed in PCT/US99/09346 (i.e., the original application underlying the Patent; published as W099/057280), 2010.
PSORT analysis of Seq ID Nos. 4 and 6, and of 'Contig295' 300mer, 2009.
PSORT prediction result for Seq ID No. 2, 2010.
Response to Communication, filed in EP Application No. 07075161.5. Oct. 28, 2009.
Rinaudo et al. (2009). "Vaccinology in the genome era", The Journal of Clinical Investigation, 119(9):2515-2525.
Romero et al. (1994). "Current status of Meningococcal group B vaccine candidates: capsular or noncapsular?" Clin. Microbiol. Rev. 7(4):559-575.
Sanger Centre's "Projects" website as of Dec. 10, 1997 as retrievable via http://web.archive.org.
Sequence for "Putative Lipoprotein [Neisseria meningitidis Z2491]," NCBI Reference Sequence: YP_002342062.1, Mar. 30, 2000.
Serruto et al. (2009). "Genome-based approaches to develop vaccines against bacterial pathogens," Vaccine 27:3245-3250.
Supplementary Declaration by Dr. Julian Parkhill, dated May 10, 2010.
Telford et al. (2003). "Genomic and Proteomics in Vaccine Design," in New Bacterial Vaccines, edited by Ellis et al. Kleweur Academic/Plenum Publishers, USA. pp. 1-11 (2 pages).
U.S. Appl. No. 60/098,685, "Neisseria Spp, Polypeptide, Gene Sequence And Uses Thereof," filed Sep. 1, 1998.
Welsch et al. (2004). "Protective Activity of Monoclonal Antibodies to Genome-Derived Neisserial Antigen 1870, a Neisseria meningitidis Candidate Vaccine," The Journal of Immunology 172: 5606-5615.
Zollinger (1997). "New and Improved Vaccines Against Meningococcal Disease" in New Generation Vaccines, 2nd Ed., edited by Levine et al., Marcel Dekker, New York. pp. 469-488.
Notice of Opposition against European Patent EP 1645631, granted on Oct. 24, 2007. Opposition filed on Jul. 23, 2008. 20 pages.
Patentees' Response to Opposition against European Patent EP 1645631, granted on Oct. 24, 2007. 13 pages.
Bjune et al., "Effect of outer membrane vesicle vaccine against group B meningococcal disease in Norway," Lancet 338(8775):1093-1096,1991.
Brandileone et al. (1994). "Induction Of Iron Regulated Proteins During Normal Growth of Neisseria meningitidis In A Chemically Defined Medium," Rev Inst Med trop Sao Paulo 36(4):301-310.
Lihui, G. et al. (1997). "Analysis of the OMP antigenicity of serogroup B meningococci," Chinese J Microbiol Immunol, Jun. 1997 (abstract only).
European Search Report dated Oct. 10, 2011 for EP Application No. 10177890.0, 11 pages.
European Search Report dated Sep. 29, 2011 for EP Application No. 10177891.8, 10 pages.
Gomez et al. (1998). "Effect of adjuvants in the isotypes of bactericidal activity of antibodies against the transferrin-binding proteins of Neisseria meningitidis," Vaccine 16(17):1633-1639.
Jennings et al. (1995) "Molecular analysis of a locus for the biosynthesis and phase-variable expression of the lacto-N-neotetraose terminal lipopolysaccharide structure in Neisseria meningitidis," Molecular Biology, 18(4):729-740.
Katial et al. (2002). "Immunogenicity and Safety Testing of a Group B Intranasal Meningococcal Native Outer Membrane Vesicle Vaccine," Infection and Immunity 70(2):702-707.

(56) References Cited

OTHER PUBLICATIONS

Partial European Search Report dated Aug. 22, 2011 for EP Application No. 10177887.6, 11 pages.
Quakyi et al., (1997) "Modulation of the biological activities of meningococcal endotoxins by association with outer membrane proteins is not inevitably linked to toxicity" Infection and Immunity 65(5):1972-1979.
Beernick (Jul. 2010) "Impaired immungenicity of a meningococcal factor H-binding protein vaccine engineered to eliminate factor h binding," Clin Vac Immunol 17(7):1074-1078.
Beernink et al (Jul. 2006). "Rapid Genetic Grouping of Factor H-Binding Protein (Genome-Derived Neisserial Antigen 1870), a Promising Group B Meningococcal Vaccine Candidate," Clinical and Vaccine Immunology 13(7):758-763.
Beernink et al. (Jun. 2008). "Bactericidal antibody responses, induced by meningococcal recombinant chimeric factor H-binding protein vaccines," Infection And Immunity 76(6):2568-2575.
Beernink et al. (Sep. 2008). "Fine antigenic specificity and cooperative bactericidal activity of monoclonal antibodies directed at the meningococcal vaccine candidate factor h-binding protein," Infection And Immunity 76(9):4232-4240.
Fontana et al. (2002). A genomic approach Abstract from the 13$^{th}$ International Pathogenic *Neisseria* Conference, Oslo, Norway, Sep. 1-6, 2002. p. 248.
Granoff, DM. (2009). Relative importance of complement-mediated bactericidal and opsonic activity for protection against meningococcal disease. Vaccine 27(Supplement 2): B117-B125.
Jiang et al., (2010) "Broad vaccine coverage predicted for a bivalent recombinant factor H binding protein based vaccine to prevent serogroup B meningococcal disease" Vaccine 28:6086-6093.
Lucidarme et al., (Sep. 16, 2009) "Characterization of fHbp, nhba (gna2132), nadA, porA, sequence type (ST), and genomic presence of IS1301 in group B meningococcal ST269 clonal complex isolates from England and Wales" Journal of Clinical Microbiology, 47(11):3577-85.
Lucidarme et al., 2010 "Characterization of fHbp, nhba (gna2132), nadA, porA, and sequence type in group B meningococcal case isolates collected in England and Wales during Jan. 2008 and potential coverage of an investigational group B meningococcal vaccine" Clinical and Vaccine Immunology 17(6):919-929.
Murphy et al., (2009) "Sequence diversity of the factor H binding protein vaccine candidate in epidemiologically relevant strains of serogroup B *Neisseria meningitidis*" J Infect Dis 200:379-389.
Pajon et al. (2010). "Frequency of factor H-binding protein modular groups and susceptibility to cross-reactive bactericidal activity in invasive meningococcal isolates" Vaccine 28:2122-2129.
Pizza et al. (2008) "Factor H-binding protein, a unique meningococcal vaccine antigen" Vaccine 26S:I46-8.
Scarselli et al. (Feb. 13, 2009). "Epitope Mapping of a Bactericidal Monoclonal Antibody against the Factor H Binding Protein of *Neisseria meningitides*," Journal Of Molecular Biology 386(1):97-108.
Schneider et al. (Apr. 16, 2009) "*Neisseria meningitidis* recruits factor H using protein mimicry of host carbohydrates," Nature 458(7240):890-893.
Serruto et al. (2010). "*Neisseria meningitidis* GNA2132, a heparin-binding protein that induces protective immunity in humans," PNAS 107(8):3770-3775.
Sierra GV, et al. (1991). "Vaccine against group B *Neisseria meningitidis*: protection trial and mass vaccination results in Cuba," NIPH Ann 14: 195-207.
Tramont, (1976) "Specificity of inhibition of epithelial cell adhesion of *Neisseria gonorrhoeae*." Infection and Immunity 14:593-595.
Welsch et al. (2007) "A novel mechanism for complement-mediated killing of encapsulated *Neisseria meningitidis* elicited by monoclonal antibodies to factor H-binding protein (genome-derived Neisserial antigen 1870)" Molecular Immunology 44(1-3):256.
Welsch et al. (Apr. 1, 2008). "Complement-dependent synergistic bactericidal activity of antibodies against factor H-binding protein, a sparsely distributed meningococcal vaccine antigen," J Infect Dis 197(7):1053-1061.
Welsch et al. (2003). "Antibody to genome-derived neisserial antigen 2132, a *Neisseria meningitidis* candidate vaccine, confers protection against bacteremia in the absence of complement-mediated bactericidal activity" Journal of Infectious Diseases 188 (11):1730-1740.

\* cited by examiner

US 8,663,656 B2

POLYPEPTIDE-VACCINES FOR BROAD PROTECTION AGAINST HYPERVIRULENT MENINGOCOCCAL LINEAGES

All documents cited herein are incorporated by reference in their entirety.

TECHNICAL FIELD

This invention is in the fields of immunology and vaccinology. In particular, it relates to antigens from *Neisseria meningitidis* (meningococcus) and their use in immunisation.

BACKGROUND ART

*N. meningitidis* is a non-motile, Gram-negative human pathogen that colonises the pharynx and causes meningitis (and, occasionally, septicaemia in the absence of meningitis). It causes both endemic and epidemic disease. Following the introduction of the conjugate vaccine against *Haemophilus influenzae*, *N. meningitidis* is the major cause of bacterial meningitis in the USA.

Based on the organism's capsular polysaccharide, various serogroups of *N. meningitidis* have been identified. Serogroup A is the pathogen most often implicated in epidemic disease in sub-Saharan Africa. Serogroups B and C are responsible for the vast majority of cases in the United States and in most developed countries. Serogroups W135 and Y are responsible for the rest of the cases in the USA and developed countries. After serogroup, classification includes serotype, serosubtype and then immunotype, and the standard nomenclature lists serogroup, serotype, serosubtype, and immunotype, each separated by a colon e.g. B:4:P1.15:L3,7,9. Within serogroup B, some lineages cause disease often (hyperinvasive), some lineages cause more severe forms of disease than others (hypervirulent), and others rarely cause disease at all. Seven hypervirulent lineages are recognised, namely subgroups I, III and IV-1, ET-5 complex, ET-37 complex, A4 cluster and lineage 3. These have been defined by multilocus enzyme electrophoresis (MLEE), but multilocus sequence typing (MLST) has also been used to classify meningococci [ref. 1].

A polysaccharide vaccine against serogroups A, C, W135 & Y has been known for many years [2, 3] but a vaccine against serogroup B has proved elusive. Vaccines based on outer-membrane vesicles have been tested [e.g. see ref. 4], but the protection afforded by these vaccines is typically restricted to the strain used to make the vaccine. There remains a need, therefore, for a broadly-effective serogroup B vaccine.

Genome sequences for meningococcal serogroups A [5] and B [6,7] have been reported, and the serogroup B sequence has been studied to identify vaccine antigens [e.g. refs. 8 to 13]. Candidate antigens have been manipulated to improve heterologous expression [refs. 14 to 16].

It is an object of the invention to provide further and improved compositions for providing immunity against meningococcal disease and/or infection, and in particular for providing broad immunity against serogroup B meningococcus.

DISCLOSURE OF THE INVENTION

Vaccines against pathogens such as hepatitis B virus, diphtheria and tetanus typically contain a single protein antigen (e.g. the HBV surface antigen, or a tetanus toxoid). In contrast, acellular whooping cough vaccines typically contain at least three *B. pertussis* proteins and the Prevenar™ pneumococcal vaccine contains seven separate conjugated saccharide antigens. Other vaccines such as cellular pertussis vaccines, the measles vaccine, the inactivated polio vaccine (IPV) and meningococcal OMV vaccines are by their very nature complex mixtures of a large number of antigens.

Whether protection against can be elicited by a single antigen, a small number of defined antigens, or a complex mixture of undefined antigens, therefore depends on the pathogen in question. The invention is based on the discovery that a small number of defined antigens is able to provide broad protection against meningococcal infection, and the invention provides a composition which, after administration to a subject, is able to induce an antibody response in that subject, wherein the antibody response is bactericidal against two or more (e.g. 2 or 3) of hypervirulent lineages A4, ET-5 and lineage 3 of *N. meningitidis* serogroup B.

Rather than consisting of a single antigen, it is preferred that the composition of the invention comprises a mixture of 10 or fewer (e.g. 9, 8, 7, 6, 5, 4, 3, 2) purified antigens, and it is particularly preferred that the composition should not include complex or undefined mixtures of antigens e.g. it is preferred not to include outer membrane vesicles in the composition.

For serogroup B meningococcus, a mixture of five defined protein antigens has been found to elicit a good protective immune response. The invention thus provides a composition comprising the following five meningococcal protein antigens: (1) a 'NadA' protein; (2) a '741' protein; (3) a '936' protein; (4) a '953' protein; and (5) a '287' protein. These antigens are referred to herein as the 'five basic antigens'.

NadA Protein

'NadA' (Neisserial adhesin A) from serogroup B of *N. meningitidis* is disclosed as protein '961' in reference 10 (SEQ IDs 2943 & 2944) and as 'NMB1994' in reference 6 (see also GenBank accession numbers: 11352904 & 7227256). A detailed description of the protein can be found in reference 17. There is no corresponding protein in serogroup A [5, 17].

When used according to the present invention, NadA may take various forms. Preferred forms of NadA are truncation or deletion variants, such as those disclosed in references 14 to 16. In particular, NadA without its C-terminal membrane anchor is preferred (e.g. deletion of residues 351-405 for strain 2996 [SEQ ID 1]), which is sometimes distinguished herein by the use of a 'C' superscript e.g. NadA$^{(C)}$. Expression of NadA without its membrane anchor domain (e.g. SEQ ID 1) in *E. coli* results in secretion of the protein into the culture supernatant with concomitant removal of its 23mer leader peptide (e.g. to leave a 327mer for strain 2996 [SEQ ID 2]). Polypeptides without their leader peptides are sometimes distinguished herein by the use of a 'NL' superscript e.g. NadA$^{(NL)}$ or NadA$^{(C)(NL)}$.

Preferred NadA sequences have 50% or more identity (e.g. 60%, 70%, 80%, 90%, 95%, 99% or more) to SEQ ID 2. This includes NadA variants (e.g. allelic variants, homologs, orthologs, paralogs, mutants, etc.). Allelic forms of NadA are shown in FIG. 9 of reference 18.

Other preferred NadA sequences comprise at least n consecutive amino acids from SEQ ID 1, wherein n is 7 or more (eg. 8, 10, 12, 14, 16, 18, 20, 25, 30, 35, 40, 50, 60, 70, 80, 90, 100, 150, 200, 250 or more). Preferred fragments comprise an epitope from NadA. Other preferred fragments lack one or more amino acids (e.g. 1, 2, 3, 4, 5, 6, 7, 8, 9, 10, 15, 20, 25 or more) from the C-terminus and/or the N-terminus of SEQ ID 1 (e.g. NadA$^{(C)}$, NadA$^{(NL)}$, NadA$^{(C)(NL)}$). Where N-terminus residues are deleted, it is preferred that the deletion should not remove the ability of NadA to adhere to human epithelial cells. A preferred fragment of SEQ ID 1 is SEQ ID 2.

Secreted NadA can conveniently be prepared in highly pure form from culture supernatant by a process comprising the steps of: concentration and diafiltration against a buffer by ultrafiltration; anionic column chromatography; hydrophobic column chromatography; hydroxylapatite ceramic column chromatography; diafiltration against a buffer; and filter sterilisation. Further details of the process are given in the examples.

NadA is preferably used in an oligomeric form (e.g. in trimeric form).

741 Protein

'741' protein from serogroup B is disclosed in reference 10 (SEQ IDs 2535 & 2536) and as 'NMB1870' in reference 6 (see also GenBank accession number GI:7227128). The corresponding protein in serogroup A [5] has GenBank accession number 7379322. 741 is naturally a lipoprotein.

When used according to the present invention, 741 protein may take various forms. Preferred forms of 741 are truncation or deletion variants, such as those disclosed in references 14 to 16. In particular, the N-terminus of 741 may be deleted up to and including its poly-glycine sequence (i.e. deletion of residues 1 to 72 for strain MC58 [SEQ ID 3]), which is sometimes distinguished herein by the use of a 'ΔG' prefix. This deletion can enhance expression. The deletion also removes 741's lipidation site.

Preferred 741 sequences have 50% or more identity (e.g. 60%, 70%, 80%, 90%, 95%, 99% or more) to SEQ ID 3. This includes 741 variants (e.g. allelic variants, homologs, orthologs, paralogs, mutants, etc.). Allelic forms of 741 can be found in SEQ IDs 1 to 22 of reference 16, and in SEQ IDs 1 to 23 of reference 19. SEQ IDs 1-299 of reference 20 give further 741 sequences.

Other preferred 741 sequences comprise at least n consecutive amino acids from SEQ ID 3, wherein n is 7 or more (eg. 8, 10, 12, 14, 16, 18, 20, 25, 30, 35, 40, 50, 60, 70, 80, 90, 100, 150, 200, 250 or more). Preferred fragments comprise an epitope from 741. Other preferred fragments lack one or more amino acids (e.g. 1, 2, 3, 4, 5, 6, 7, 8, 9, 10, 15, 20, 25 or more) from the C-terminus and/or the N-terminus of SEQ OD 3.

Protein 741 is an extremely effective antigen for eliciting anti-meningococcal antibody responses, and it is expressed across all meningococcal serogroups. Phylogenetic analysis shows that the protein splits into two groups, and that one of these splits again to give three variants in total [21], and while serum raised against a given variant is bactericidal within the same variant group, it is not active against strains which express one of the other two variants i.e. there is intra-variant cross-protection, but not inter-variant cross-protection. For maximum cross-strain efficacy, therefore, it is preferred that a composition should include more than one variant of protein 741. An exemplary sequence from each variant is given in SEQ ID 10, 11 and 12 herein, starting with a N-terminal cysteine residue to which a lipid will be covalently attached in the lipoprotein form of 741.

It is therefore preferred that the composition should include at least two of: (1) a first protein, comprising an amino acid sequence having at least a % sequence identity to SEQ ID 10 and/or comprising an amino acid sequence consisting of a fragment of at least x contiguous amino acids from SEQ ID 10; (2) a second protein, comprising an amino acid sequence having at least b % sequence identity to SEQ ID 11 and/or comprising an amino acid sequence consisting of a fragment of at least y contiguous amino acids from SEQ ID 11; and (3) a third protein, comprising an amino acid sequence having at least c % sequence identity to SEQ ID 12 and/or comprising an amino acid sequence consisting of a fragment of at least z contiguous amino acids from SEQ ID 12.

The value of a is at least 85 e.g. 86, 87, 88, 89, 90, 91, 92, 93, 94, 95, 96, 97, 98, 99, 99.5, or more. The value of b is at least 85 e.g. 86, 87, 88, 89, 90, 91, 92, 93, 94, 95, 96, 97, 98, 99, 99.5, or more. The value of c is at least 85 e.g. 86, 87, 88, 89, 90, 91, 92, 93, 94, 95, 96, 97, 98, 99, 99.5, or more. The values of a, b and c are not intrinsically related to each other.

The value of x is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of y is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of z is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The values of x, y and z are not intrinsically related to each other.

It is preferred that any given 741 amino acid sequence will not fall into more than one of categories (1), (2) and (3). Any given 741 sequence will thus fall into only one of categories (1), (2) and (3). It is thus preferred that: protein (1) has less than i % sequence identity to protein (2); protein (1) has less than j % sequence identity to protein (3); and protein (2) has less than k % sequence identity to protein (3). The value of i is 60 or more (e.g. 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, etc.) and is at most a. The value of j is 60 or more (e.g. 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, etc.) and is at most b. The value of k is 60 or more (e.g. 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, etc.) and is at most c. The values of i, j and k are not intrinsically related to each other.

936 Protein

'936' protein from serogroup B is disclosed in reference 10 (SEQ IDs 2883 & 2884) and as 'NMB2091' in reference 6 (see also GenBank accession number GI:7227353). The corresponding gene in serogroup A [5] has GenBank accession number 7379093.

When used according to the present invention, 936 protein may take various forms. Preferred forms of 936 are truncation or deletion variants, such as those disclosed in references 14 to 16. In particular, the N-terminus leader peptide of 936 may be deleted (i.e. deletion of residues 1 to 23 for strain MC58 [SEQ ID 4]) to give $936^{(NL)}$.

Preferred 936 sequences have 50% or more identity (e.g. 60%, 70%, 80%, 90%, 95%, 99% or more) to SEQ ID 4. This includes variants (e.g. allelic variants, homologs, orthologs, paralogs, mutants etc).

Other preferred 936 sequences comprise at least n consecutive amino acids from SEQ ID 4, wherein n is 7 or more (eg. 8, 10, 12, 14, 16, 18, 20, 25, 30, 35, 40, 50, 60, 70, 80, 90, 100, 150, 200, 250 or more). Preferred fragments comprise an epitope from 936. Other preferred fragments lack one or more amino acids (e.g. 1, 2, 3, 4, 5, 6, 7, 8, 9, 10, 15, 20, 25 or more) from the C-terminus and/or the N-terminus of SEQ ID 4.

953 Protein

'953' protein from serogroup B is disclosed in reference 10 (SEQ IDs 2917 & 2918) and as 'NMB1030' in reference 6 (see also GenBank accession number GI:7226269). The corresponding protein in serogroup A [5] has GenBank accession number 7380108.

When used according to the present invention, 953 protein may take various forms. Preferred forms of 953 are truncation or deletion variants, such as those disclosed in references 14 to 16. In particular, the N-terminus leader peptide of 953 may be deleted (i.e. deletion of residues 1 to 19 for strain MC58 [SEQ ID 5]) to give 953$^{(NL)}$.

Preferred 953 sequences have 50% or more identity (e.g. 60%, 70%, 80%, 90%, 95%, 99% or more) to SEQ ID 5. This includes 953 variants (e.g. allelic variants, homologs, orthologs, paralogs, mutants, etc.). Allelic forms of 953 can be seen in FIG. 19 of reference 12.

Other preferred 953 sequences comprise at least n consecutive amino acids from SEQ ID 5, wherein n is 7 or more (eg. 8, 10, 12, 14, 16, 18, 20, 25, 30, 35, 40, 50, 60, 70, 80, 90, 100, 150, 200, 250 or more). Preferred fragments comprise an epitope from 953. Other preferred fragments lack one or more amino acids (e.g. 1, 2, 3, 4, 5, 6, 7, 8, 9, 10, 15, 20, 25 or more) from the C-terminus and/or the N-terminus of SEQ ID 5.

287 Protein

'287' protein from serogroup B is disclosed in reference 10 (SEQ IDs 3103 & 3104), as 'NMB2132' in reference 6, and as 'GNA2132' in reference 13 (see also GenBank accession number GI:7227388). The corresponding protein in serogroup A [5] has GenBank accession number 7379057.

When used according to the present invention, 287 protein may take various forms. Preferred forms of 287 are truncation or deletion variants, such as those disclosed in references 14 to 16. In particular, the N-terminus of 287 may be deleted up to and including its poly-glycine sequence (i.e. deletion of residues 1 to 24 for strain MC58 [SEQ ID 6]), which is sometimes distinguished herein by the use of a 'ΔG' prefix. This deletion can enhance expression.

Preferred 287 sequences have 50% or more identity (e.g. 60%, 70%, 80%, 90%, 95%, 99% or more) to SEQ ID 6. This includes 287 variants (e.g. allelic variants, homologs, orthologs, paralogs, mutants, etc.). Allelic forms of 287 can be seen in FIGS. 5 and 15 of reference 12, and in example 13 and FIG. 21 of reference 10 (SEQ IDs 3179 to 3184).

Other preferred 287 sequences comprise at least n consecutive amino acids from SEQ ID 6, wherein n is 7 or more (eg. 8, 10, 12, 14, 16, 18, 20, 25, 30, 35, 40, 50, 60, 70, 80, 90, 100, 150, 200, 250 or more). Preferred fragments comprise an epitope from 287. Other preferred fragments lack one or more amino acids (e.g. 1, 2, 3, 4, 5, 6, 7, 8, 9, 10, 15, 20, 25 or more) from the C-terminus and/or the N-terminus of SEQ ID 6.

Fusion Proteins

The five antigens may be present in the composition as five separate proteins, but it is preferred that at least two of the antigens are expressed as a single polypeptide chain (a 'hybrid' protein [refs. 14 to 16]) e.g. such that the five antigens form fewer than five polypeptides. Hybrid proteins offer two principal advantages: first, a protein that may be unstable or poorly expressed on its own can be assisted by adding a suitable hybrid partner that overcomes the problem; second, commercial manufacture is simplified as only one expression and purification need be employed in order to produce two separately-useful proteins.

A hybrid protein included in a composition of the invention may comprise two or more (i.e. 2, 3, 4 or 5) of the five basic antigens. Hybrids consisting of two of the five basic antigens are preferred.

Within the combination of five basic antigens, an antigen may be present in more than one hybrid protein and/or as a non-hybrid protein. It is preferred, however, that an antigen is present either as a hybrid or as a non-hybrid, but not as both, although it may be useful to include protein 741 both as a hybrid and a non-hybrid (preferably lipoprotein) antigen, particularly where more than one variant of 741 is used.

Two-antigen hybrids for use in the invention comprise: NadA & 741; NadA & 936; NadA & 953; NadA & 287; 741 & 936; 741 & 953; 741 & 287; 936 & 953; 936 & 287; 953 & 287. Preferred two-antigen hybrids comprise: 741 & 936; 953 & 287.

Hybrid proteins can be represented by the formula $NH_2$-A-[-X-L-]$_n$-B—COOH, wherein: X is an amino acid sequence of one of the five basic antigens; L is an optional linker amino acid sequence; A is an optional N-terminal amino acid sequence; B is an optional C-terminal amino acid sequence; and n is 2, 3, 4 or 5.

If a —X— moiety has a leader peptide sequence in its wild-type form, this may be included or omitted in the hybrid protein. In some embodiments, the leader peptides will be deleted except for that of the —X— moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of [—X-L-], linker amino acid sequence -L- may be present or absent. For instance, when n=2 the hybrid may be $NH_2$—$X_1$-$L_1$-$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, etc. Linker amino acid sequence(s) -L- will typically be short (e.g. 20 or fewer amino acids i.e. 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising Gly$_n$ where n=2, 3, 4, 5, 6, 7, 8, 9, 10 or more), and histidine tags (i.e. His$_n$ where n=3, 4, 5, 6, 7, 8, 9, 10 or more). Other suitable linker amino acid sequences will be apparent to those skilled in the art. A useful linker is GSGGGG (SEQ ID 9), with the Gly-Ser dipeptide being formed from a BamHI restriction site, thus aiding cloning and manipulation, and the (Gly)$_4$ tetrapeptide being a typical poly-glycine linker. If $X_{n+1}$ is a ΔG protein and $L_n$ is a glycine linker, this may be equivalent to $X_{n+1}$ not being a ΔG protein and $L_n$ being absent.

-A- is an optional N-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. His$_n$ where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine.

—B— is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. His$_n$ where n=3, 4, 5, 6, 7, 8, 9, 10 or more), or sequences which enhance protein stability. Other suitable C-terminal amino acid sequences will be apparent to those skilled in the art.

Most preferably, n is 2. Two preferred proteins of this type are: $X_1$ is a 936 and $X_2$ is a 741; $X_1$ is a 287 and $X_2$ is a 953.

Two particularly preferred hybrid proteins of the invention are as follows:

| n | A | $X_1$ | $L_1$ | $X_2$ | $L_2$ | B | [SEQ ID] |
|---|---|---|---|---|---|---|---|
| 2 | MA | ΔG287 | GSGGGG | $936^{(NL)}$ | — | — | 7 |
| 2 | M | $936^{(NL)}$ | GSGGGG | ΔG741 | — | — | 8 |

These two proteins may be used in combination with NadA (particularly with SEQ ID 2).

936-ΔG741 hybrid can conveniently be prepared in highly pure form from expression in *E. coli* by a process comprising the steps of: homogenisation; centrifugation; cationic column chromatography; anionic column chromatography; hydrophobic column chromatography; diafiltration against a buffer; and filter sterilisation. Further details of the process are given in the examples.

Sequences

The invention provides a polypeptide having an amino acid sequence selected from the group consisting of SEQ IDs 1 to 8. It also provides polypeptides having an amino acid sequence with sequence identity to an amino acid sequence selected from the group consisting of SEQ IDs 1 to 8. As described above, the degree of sequence identity is preferably greater than 50% (eg. 60%, 70%, 80%, 90%, 95%, 99% or more).

The invention also provides a polypeptide comprising a fragment of a *N. meningitidis* NadA sequence, wherein said fragment retains the ability of NadA to adhere to human epithelial cells. Fragments which retain amino acids 24-87 of full-length NadA are thus preferred. Preferred fragments lack the N-terminus leader peptide of said NadA and/or the C-terminus membrane anchor domain of said NadA. This invention does not include within its scope any of the NadA fragments disclosed in the prior art e.g. in references 6 to 18. With reference to full-length NadA [17], SEQ ID 1 lacks the membrane anchor domain, and SEQ ID 2 lacks the leader peptide.

The invention also provides nucleic acid encoding such polypeptides. Furthermore, the invention provides nucleic acid which can hybridise to this nucleic acid, preferably under "high stringency" conditions (e.g. 65° C. in a 0.1×SSC, 0.5% SDS solution).

Polypeptides of the invention can be prepared by various means (e.g. recombinant expression, purification from cell culture, chemical synthesis (at least in part), etc.) and in various forms (e.g. native, fusions, non-glycosylated, lipidated, etc.). They are preferably prepared in substantially pure form (i.e. substantially free from other *N. meningitidis* or host cell proteins).

Nucleic acid according to the invention can be prepared in many ways (e.g. by chemical synthesis (at least in part), from genomic or cDNA libraries, from the organism itself, etc.) and can take various forms (e.g. single stranded, double stranded, vectors, probes, etc.). They are preferably prepared in substantially pure form (i.e. substantially free from other *N. meningitidis* or host cell nucleic acids).

The term "nucleic acid" includes DNA and RNA, and also their analogues, such as those containing modified backbones (e.g. phosphorothioates, etc.), and also peptide nucleic acids (PNA) etc. The invention includes nucleic acid comprising sequences complementary to those described above (eg. for antisense or probing purposes).

The invention also provides a process for producing a polypeptide of the invention, comprising the step of culturing a host cell transformed with nucleic acid of the invention under conditions which induce polypeptide expression.

The invention provides a process for producing a polypeptide of the invention, comprising the step of synthesising at least part of the polypeptide by chemical means.

The invention provides a process for producing nucleic acid of the invention, comprising the step of amplifying nucleic acid using a primer-based amplification method (e.g. PCR).

The invention provides a process for producing nucleic acid of the invention, comprising the step of synthesising at least part of the nucleic acid by chemical means.

Strains

Preferred proteins of the invention comprise an amino acid sequence found in *N. meningitidis* serogroup B. Within serogroup B, preferred strains are 2996, MC58, 95N477, and 394/98. Strain 394/98 is sometimes referred to herein as 'NZ', as it is a New Zealand strain.

Protein 287 is preferably from strain 2996 or, more preferably, from strain 394/98.

Protein 741 is preferably from serogroup B strains MC58, 2996, 394/98, or 95N477, or from serogroup C strain 90/18311. Strain MC58 is more preferred.

Proteins 936, 953 and NadA are preferably from strain 2996.

Strains may be indicated as a subscript e.g. $741_{MC58}$ is protein 741 from strain MC58. Unless otherwise stated, proteins mentioned herein (e.g. with no subscript) are from *N. meningitidis* strain 2996, which can be taken as a 'reference' strain. It will be appreciated, however, that the invention is not in general limited by strain. As mentioned above, general references to a protein (e.g. '287', '919' etc.) may be taken to include that protein from any strain. This will typically have sequence identity to 2996 of 90% or more (eg. 91%, 92%, 93%, 94%, 95%, 96%, 97%, 98%, 99% or more).

Where a composition includes a particular protein antigen (e.g. 741 or 287), the composition can include that antigen in more than one variant form e.g. the same protein, but from more than one strain. These proteins may be included as tandem or separate proteins.

Where hybrid proteins are used, the individual antigens within the hybrid (i.e. individual —X— moieties) may be from one or more strains. Where n=2, for instance, $X_2$ may be from the same strain as $X_1$ or from a different strain. Where n=3, the strains might be (i) $X_1=X_2=X_3$ (ii) $X_1=X_2\neq X_3$ (iii) $X_1\neq X_2=X_3$ (iv) $X_1\neq X_2\neq X_3$ or (v) $X_1=X_3\neq X_2$, etc.

Hypervirulent Lineages and Bactericidal Antibody Responses

In general, compositions of the invention are able to induce serum bactericidal antibody responses after being administered to a subject. These responses are conveniently measured in mice and are a standard indicator of vaccine efficacy [e.g. see end-note 14 of reference 13]. Serum bactericidal activity (SBA) measures bacterial killing mediated by complement, and can be assayed using human or baby rabbit complement. WHO standards require a vaccine to induce at least a 4-fold rise in SBA in more than 90% of recipients.

Rather than offering narrow protection, compositions of the invention can induce bactericidal antibody responses against more than one hypervirulent lineage of serogroup B. In particular, they can induce bactericidal responses against two or three of the following three hypervirulent lineages: (i) cluster A4; (ii) ET5 complex; and (iii) lineage 3. They may additionally induce bactericidal antibody responses against one or more of hypervirulent lineages subgroup I, subgroup III, subgroup IV-1 or ET-37 complex, and against other lineages e.g. hyperinvasive lineages.

This does not necessarily mean that the composition can induce bactericidal antibodies against each and every strain of serogroup B meningococcus within these hypervirulent lineages e.g. rather, for any given group of four of more strains of serogroup B meningococcus within a particular hypervirulent lineage, the antibodies induced by the composition are bactericidal against at least 50% (e.g. 60%, 70%, 80%, 90% or more) of the group. Preferred groups of strains will include strains isolated in at least four of the following countries: GB, AU, CA, NO, IT, US, NZ, NL, BR, and CU. The serum preferably has a bactericidal titre of at least 1024 (e.g. $2^{10}$, $2^{11}$, $2^{12}$, $2^{13}$, $2^{14}$, $2^{15}$, $2^{16}$, $2^{17}$, $2^{18}$ or higher, preferably at least $2^{14}$) i.e. the serum is able to kill at least 50% of test bacteria of a particular strain when diluted 1/1024, as described in reference 13.

Preferred compositions can induce bactericidal responses against the following strains of serogroup B meningococcus: (i) from cluster A4, strain 961-5945 (B:2b:P1.21,16) and/or strain G2136 (B:-); (ii) from ET-5 complex, strain MC58 (B:15:P1.7,16b) and/or strain 44/76 (B:15:P1.7,16); (iii) from lineage 3, strain 394/98 (B:4:P1.4) and/or strain BZ198 (B:NT:-). More preferred compositions can induce bactericidal responses against strains 961-5945, 44/76 and 394/98.

Strains 961-5945 and G2136 are both *Neisseria* MLST reference strains [ids 638 & 1002 in ref. 22]. Strain MC58 is widely available (e.g. ATCC BAA-335) and was the strain sequenced in reference 6. Strain 44/76 has been widely used and characterised (e.g. ref 23) and is one of the *Neisseria* MLST reference strains [id 237 in ref. 22; row 32 of Table 2 in ref. 1]. Strain 394/98 was originally isolated in New Zealand in 1998, and there have been several published studies using this strain (e.g. refs. 24 & 25). Strain BZ198 is another MLST reference strain [id 409 in ref. 22; row 41 of Table 2 in ref. 1].

The composition may additionally induce a bactericidal response against serogroup W135 strain LNP17592 (W135: 2a:P1.5,2), from ET-37 complex. This is a Haji strain isolated in France in 2000.

Heterologous Host

Whilst expression of the proteins of the invention may take place in *Neisseria*, the present invention preferably utilises a heterologous host. The heterologous host may be prokaryotic (e.g. a bacterium) or eukaryotic. It is preferably *E. coli*, but other suitable hosts include *Bacillus subtilis, Vibrio cholerae, Salmonella typhi, Salmonella typhimurium, Neisseria lactamica, Neisseria cinerea, Mycobacteria* (e.g. *M. tuberculosis*), yeast, etc.

Thus the invention provides a composition which, after administration to a subject, is able to induce an antibody response in that subject, wherein the antibody response is bactericidal against two or more (e.g. 2 or 3) of hypervirulent lineages A4, ET-5 and lineage 3 of *N. meningitidis* serogroup B, and wherein the immunogens in the composition which give rise to the antibody response are obtained by recombinant expression in a non-Neisserial host. Thus the immunogens in the compositions of the invention are preferably recombinant immunogens. Compositions which do not include OMV preparations may thus be preferred.

Immunogenic Compositions and Medicaments

Compositions of the invention are immunogenic, and are more preferably vaccine compositions. Vaccines according to the invention may either be prophylactic (i.e. to prevent infection) or therapeutic (i.e. to treat infection), but will typically be prophylactic.

The pH of the composition is preferably between 6 and 8, preferably about 7. Stable pH may be maintained by the use of a buffer. Where a composition comprises an aluminium hydroxide salt, it is preferred to use a histidine buffer [26]. The composition may be sterile and/or pyrogen-free. Compositions of the invention may be isotonic with respect to humans.

Compositions may be presented in vials, or they may be presented in ready-filled syringes. The syringes may be supplied with or without needles. A syringe will include a single dose of the composition, whereas a vial may include a single dose or multiple doses. Injectable compositions will usually be liquid solutions or suspensions. Alternatively, they may be presented in solid form (e.g. freeze-dried) for solution or suspension in liquid vehicles prior to injection.

Compositions of the invention may be packaged in unit dose form or in multiple dose form. For multiple dose forms, vials are preferred to pre-filled syringes. Effective dosage volumes can be routinely established, but a typical human dose of the composition for injection has a volume of 0.5 ml.

Where a composition of the invention is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

The invention also provides a composition of the invention for use as a medicament. The medicament is preferably able to raise an immune response in a mammal (i.e. it is an immunogenic composition) and is more preferably a vaccine.

The invention also provides the use of a composition of the invention in the manufacture of a medicament for raising an immune response in a mammal. It also provides the use of a 'NadA' protein, a '741' protein, a '936' protein, a '953' protein, and a '287' protein (and other optional antigens) in the manufacture of a medicament for raising an immune response in a mammal. The medicament is preferably a vaccine.

The invention also provides a method for raising an immune response in a mammal comprising the step of administering an effective amount of a composition of the invention. The immune response is preferably protective and preferably involves antibodies. The method may raise a booster response.

The mammal is preferably a human. Where the vaccine is for prophylactic use, the human is preferably a child (e.g. a toddler or infant); where the vaccine is for therapeutic use, the human is preferably an adult. A vaccine intended for children may also be administered to adults e.g. to assess safety, dosage, immunogenicity, etc.

These uses and methods are preferably for the prevention and/or treatment of a disease caused by a *Neisseria* (e.g. meningitis, septicaemia, bacteremia, gonorrhoea etc.). The prevention and/or treatment of bacterial or meningococcal meningitis is preferred.

One way of checking efficacy of therapeutic treatment involves monitoring Neisserial infection after administration of the composition of the invention. One way of checking efficacy of prophylactic treatment involves monitoring immune responses against the five basic antigens after administration of the composition. Immunogenicity of compositions of the invention can be determined by administering them to test subjects (e.g. children 12-16 months age, or animal models [27]) and then determining standard parameters including serum bactericidal antibodies (SBA) and ELISA titres (GMT) of total and high-avidity anti-capsule IgG. These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

Neisserial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition). The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 28 & 29]. Success with nasal administration of pneumococcal saccharides [30,31], pneumococcal polypeptides [32], Hib saccharides [33], MenC saccharides [34], and mixtures of Hib and MenC saccharide conjugates [35] has been reported.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials, and a typical quantity of each meningococcal saccharide antigen per dose is between 1 µg and 20 µg e.g. about 1 µg, about 2.5 µg, about 4 µg, about 5 µg, or about 10 µg (expressed as saccharide).

Further Non-Antigen Components of the Composition

The composition of the invention will typically, in addition to the components mentioned above, comprise one or more 'pharmaceutically acceptable carriers', which include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose [36], trehalose [37], lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in reference 38.

Compositions of the invention may include an antimicrobial, particularly when packaged in multiple dose format.

Compositions of the invention may comprise detergent e.g. a TWEEN™ (polysorbate), such as TWEEN 80™. Detergents are generally present at low levels e.g. <0.01%.

Compositions of the invention may include sodium salts (e.g. sodium chloride) to give tonicity. A concentration of 10±2 mg/ml NaCl is typical.

Compositions of the invention will generally include a buffer. A phosphate buffer is typical.

Compositions of the invention may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilised material. The pH of a composition for lyophilisation may be adjusted to around 6.1 prior to lyophilisation.

Vaccines of the invention may be administered in conjunction with other immunoregulatory agents. In particular, compositions will usually include an adjuvant. Adjuvants which may be used in compositions of the invention include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 39], or mixtures of different mineral compounds, with the compounds taking any suitable form (e.g. gel, crystalline, amorphous, etc.), and with adsorption being preferred. The mineral containing compositions may also be formulated as a particle of metal salt [40].

Aluminium phosphates are particularly preferred, particularly in compositions which include a *H. influenzae* saccharide antigen, and a typical adjuvant is amorphous aluminium hydroxyphosphate with $PO_4$/Al molar ratio between 0.84 and 0.92, included at 0.6 mg $Al^{3+}$/ml. Adsorption with a low dose of aluminium phosphate may be used e.g. between 50 and 100 µg $Al^{3+}$ per conjugate per dose. Where there is more than one conjugate in a composition, not all conjugates need to be adsorbed.

B. Oil Emulsions

Oil emulsion compositions suitable for use as adjuvants in the invention include squalene-water emulsions, such as MF59 [Chapter 10 of ref. 39; see also ref. 41] (5% Squalene, 0.5% TWEEN 80™, and 0.5% Span 85, formulated into submicron particles using a microfluidizer). Complete Freund's adjuvant (CFA) and incomplete Freund's adjuvant (IFA) may also be used.

C. Saponin Formulations [Chapter 22 of Ref 39]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 42. Saponin formulations may also comprise a sterol, such as cholesterol [43].

Combinations of saponins and cholesterols can be used to form unique particles called immunostimulating complexs (ISCOMs) [chapter 23 of ref. 39]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 43-45. Optionally, the ISCOMS may be devoid of additional detergent [46].

A review of the development of saponin based adjuvants can be found in refs. 47 & 48.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 49-54. Virosomes are discussed further in, for example, ref. 55

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 56. Such "small particles" of 3dMPL are small enough to be sterile filtered through a 0.22 μm membrane [56]. Other non-toxic LPS derivatives include monophosphoryl lipid A mimics, such as aminoalkyl glucosaminide phosphate derivatives e.g. RC-529 [57,58].

Lipid A derivatives include derivatives of lipid A from *Escherichia coli* such as OM-174. OM-174 is described for example in refs. 59 & 60.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 61, 62 and 63 disclose possible analog substitutions e.g. replacement of guanosine with 2'-deoxy-7-deazaguanosine. The adjuvant effect of CpG oligonucleotides is further discussed in refs. 64-69.

The CpG sequence may be directed to TLR9, such as the motif GTCGTT or TTCGTT [70]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 71-73. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 70 & 74-76.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 77 and as parenteral adjuvants in ref. 78. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivaties thereof, particularly LT-K63 and LT-R72, as adjuvants can be found in refs. 79-86. Numerical reference for amino acid substitutions is preferably based on the alignments of the A and B subunits of ADP-ribosylating toxins set forth in ref. 87, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [88], etc.) [89], interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [90] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [91].

H. Microparticles

Microparticles may also be used as adjuvants in the invention. Microparticles (i.e. a particle of ~100 nm to ~150 μm diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref 39)

Examples of liposome formulations suitable for use as adjuvants are described in refs. 92-94.

J. Polyoxyethylene Ether and Polyoxyethylene Ester-Formulations

Adjuvants suitable for use in the invention include polyoxyethylene ethers and polyoxyethylene esters [95]. Such formulations further include polyoxyethylene sorbitan ester surfactants in combination with an octoxynol [96] as well as polyoxyethylene alkyl ethers or ester surfactants in combination with at least one additional non-ionic surfactant such as an octoxynol [97]. Preferred polyoxyethylene ethers are selected from the following group: polyoxyethylene-9-lauryl ether (laureth 9), polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 98 and 99.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1',2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 100 and 101.

The invention may also comprise combinations of aspects of one or more of the adjuvants identified above. For example, the following adjuvant compositions may be used in the invention: (1) a saponin and an oil-in-water emulsion [102]; (2) a saponin (e.g. QS21)+a non-toxic LPS derivative (e.g. 3 dMPL) [103]; (3) a saponin (e.g. QS21)+a non-toxic LPS derivative (e.g. 3 dMPL)+a cholesterol; (4) a saponin (e.g. QS21)+3 dMPL+IL 12 (optionally+a sterol) [104]; (5) combinations of 3 dMPL with, for example, QS21 and/or oil-in-water emulsions [105]; (6) SAF, containing 10% squalane, 0.4% TWEEN 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% TWEEN 80™, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3 dMPL).

Other substances that act as immunostimulating agents are disclosed in chapter 7 of ref. 39.

The use of an aluminium hydroxide or aluminium phosphate adjuvant is particularly preferred, and antigens are generally adsorbed to these salts. Aluminium hydroxide is preferably avoided as an adjuvant if the composition includes a Hib antigen. Where an aluminium phosphate it used and desired not to adsorb an antigen to the adjuvant, this is favoured by including free phosphate ions in solution (e.g. by the use of a phosphate buffer). Prevention of adsorption can also be achieved by selecting the correct pH during antigen/adjuvant mixing, an adjuvant with an appropriate point of zero charge, and an appropriate order of mixing for different antigens in a composition [106].

Calcium phosphate is another preferred adjuvant.

Further Antigens

Compositions of the invention contain five basic meningococcal protein antigens. They may also include further antigens, although it may contain no meningococcal protein antigens other than the five basic antigens. Further antigens for inclusion may be, for example:

- a saccharide antigen from *Haemophilus influenzae* B.
- a saccharide antigen from *N. meningitidis* serogroup A, C, W135 and/or Y, such as the oligosaccharide disclosed in ref. 107 from serogroup C or the oligosaccharides of ref. 108.
- a saccharide antigen from *Streptococcus pneumoniae* [e.g. 155, 156 157].
- an antigen from hepatitis A virus, such as inactivated virus [e.g. 109, 110].
- an antigen from hepatitis B virus, such as the surface and/or core antigens [e.g. 110, 111].
- a diphtheria antigen, such as a diphtheria toxoid [e.g. chapter 3 of ref. 112] e.g. the $CRM_{197}$ mutant [e.g. 113].
- a tetanus antigen, such as a tetanus toxoid [e.g. chapter 4 of ref. 112].
- an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 114 & 115]. Cellular pertussis antigen may be used.
- an outer-membrane vesicle (OMV) preparation from *N. meningitidis* serogroup B, such as those disclosed in refs. 4, 116, 117, 118 etc.
- polio antigen(s) [e.g. 119, 120] such as OPV or, preferably, IPV.

The composition may comprise one or more of these further antigens. Antigens will typically be present at a concentration of at least 11 g/ml each. In general, the concentration of any given antigen will be sufficient to elicit an immune response against that antigen. It is preferred that the protective efficacy of individual saccharide antigens is not removed by combining them, although actual immunogenicity (e.g. ELISA titres) may be reduced.

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. Such DTP combinations can be used to reconstitute lyophilised conjugates.

Where a saccharide or carbohydrate antigen is used, it is preferably conjugated to a carrier protein in order to enhance immunogenicity (see below).

Toxic protein antigens may be detoxified where necessary (e.g. detoxification of pertussis toxin by chemical and/or genetic means [115]).

As an alternative to using protein antigens in the composition of the invention, nucleic acid encoding the antigen may be used [e.g. refs. 121 to 129]. Protein components of the compositions of the invention may thus be replaced by nucleic acid (preferably DNA e.g. in the form of a plasmid) that encodes the protein. Similarly, compositions of the invention may comprise proteins which mimic saccharide antigens e.g. mimotopes [130] or anti-idiotype antibodies. These may replace individual saccharide components, or may supplement them. As an example, the vaccine may comprise a peptide mimic of the MenC [131] or the MenA [132] capsular polysaccharide in place of the saccharide itself.

Particularly preferred compositions of the invention include one, two or three of: (a) saccharide antigens from meningococcus serogroups Y, W135, C and (optionally) A; (b) a saccharide antigen from *Haemophilus influenzae* type B; and/or (c) an antigen from *Streptococcus pneumoniae*. A composition comprising the serogroup B antigens and a Hib conjugate is particularly preferred.

Meningococcus Serogroups Y, W135, C and (Optionally) A

As mentioned above, polysaccharide vaccines against serogroups A, C, W135 & Y has been known for many years. These vaccines (MENCEVAX ACWY™ and MENOMUNE™) are based on the organisms' capsular polysaccharides and, although they are effective in adolescents and adults, they give a poor immune response and short duration of protection, and they cannot be used in infants.

In contrast to the unconjugated polysaccharide antigens in these vaccines, the recently-approved serogroup C vaccines (Menjugate™ [133,107], Meningitec™ and NeisVac-C™) include conjugated saccharides. Menjugate™ and Meningitec™ have oligosaccharide antigens conjugated to a $CRM_{197}$ carrier, whereas NeisVac-C™ uses the complete polysaccharide (de-O-acetylated) conjugated to a tetanus toxoid carrier.

Compositions of the present invention preferably include capsular saccharide antigens from one or more of meningococcus serogroups Y, W135, C and (optionally) A, wherein the antigens are conjugated to carrier protein(s) and/or are oligosaccharides.

A typical quantity of each meningococcal saccharide antigen per dose is between 1 μg and 20 μg e.g. about 1 μg, about 2.5 μg, about 4 μg, about 5 μg, or about 10 μg (expressed as saccharide).

Where a mixture comprises capsular saccharides from both serogroups A and C, the ratio (w/w) of MenA saccharide:MenC saccharide may be greater than 1 (e.g. 2:1, 3:1, 4:1, 5:1, 10:1 or higher). Where a mixture comprises capsular saccharides from serogroup Y and one or both of serogroups C and W135, the ratio (w/w) of MenY saccharide:MenW135 saccharide may be greater than 1 (e.g. 2:1, 3:1, 4:1, 5:1, 10:1 or higher) and/or that the ratio (w/w) of MenY saccharide:MenC saccharide may be less than 1 (e.g. 1:2, 1:3, 1:4, 1:5, or lower). Preferred ratios (w/w) for saccharides from serogroups A:C:W135:Y are: 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1. Preferred ratios (w/w) for saccharides from serogroups C:W135:Y are: 1:1:1; 1:1:2; 1:1:1; 2:1:1; 4:2:1; 2:1:2; 4:1:2; 2:2:1; and 2:1:1. Using a substantially equal mass of each saccharide is preferred.

Capsular saccharides will generally be used in the form of oligosaccharides. These are conveniently formed by fragmentation of purified capsular polysaccharide (e.g. by hydrolysis), which will usually be followed by purification of the fragments of the desired size.

Fragmentation of polysaccharides is preferably performed to give a final average degree of polymerisation (DP) in the oligosaccharide of less than 30 (e.g. between 10 and 20, preferably around 10 for serogroup A; between 15 and 25 for serogroups W135 and Y, preferably around 15-20; between 12 and 22 for serogroup C; etc.). DP can conveniently be measured by ion exchange chromatography or by colorimetric assays [134].

If hydrolysis is performed, the hydrolysate will generally be sized in order to remove short-length oligosaccharides [135]. This can be achieved in various ways, such as ultrafiltration followed by ion-exchange chromatography. Oligosaccharides with a degree of polymerisation of less than or equal to about 6 are preferably removed for serogroup A, and those less than around 4 are preferably removed for serogroups W135 and Y.

Preferred MenC saccharide antigens are disclosed in reference 133, as used in Menjugate™.

The saccharide antigen may be chemically modified. This is particularly useful for reducing hydrolysis for serogroup A [136; see below]. De-O-acetylation of meningococcal saccharides can be performed. For oligosaccharides, modification may take place before or after depolymerisation.

Where a composition of the invention includes a MenA saccharide antigen, the antigen is preferably a modified saccharide in which one or more of the hydroxyl groups on the native saccharide has/have been replaced by a blocking group [136]. This modification improves resistance to hydrolysis, and means that the serogroup A antigen can be stored and used in a liquid formulation rather than requiring lyophilisation.

The number of monosaccharide units having blocking groups can vary. For example, all or substantially all the monosaccharide units may have blocking groups. Alternatively, at least 10%, 20%, 30%, 40%, 50%, 60%, 70%, 80% or 90% of the monosaccharide units may have blocking groups. At least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 monosaccharide units may have blocking groups.

Likewise, the number of blocking groups on a monosaccharide unit may vary. For example, the number of blocking groups on a monosaccharide unit may be 1 or 2. The blocking group will generally be at the 4 position and/or 3-position of the monosaccharide units.

The terminal monosaccharide unit may or may not have a blocking group instead of its native hydroxyl. It is preferred to retain a free anomeric hydroxyl group on a terminal monosaccharide unit in order to provide a handle for further reactions (e.g. conjugation). Anomeric hydroxyl groups can be converted to amino groups ($-NH_2$ or $-NH\text{-}E$, where E is a nitrogen protecting group) by reductive amination (using, for example, $NaBH_3CN/NH_4Cl$), and can then be regenerated after other hydroxyl groups have been converted to blocking groups.

Blocking groups to replace hydroxyl groups may be directly accessible via a derivatizing reaction of the hydroxyl group i.e. by replacing the hydrogen atom of the hydroxyl group with another group. Suitable derivatives of hydroxyl groups which act as blocking groups are, for example, carbamates, sulfonates, carbonates, esters, ethers (e.g. silyl ethers or alkyl ethers) and acetals. Some specific examples of such blocking groups are allyl, Aloc, benzyl, BOM, t-butyl, trityl, TBS, TBDPS, TES, TMS, TIPS, PMB, MEM, MOM, MTM, THP, etc. Other blocking groups that are not directly accessible and which completely replace the hydroxyl group include $C_{1-12}$ alkyl, $C_{3-12}$ alkyl, $C_{5-12}$ aryl, $C_{5-12}$ aryl-$C_{1-6}$ alkyl, $NR^1R^2$ ($R^1$ and $R^2$ are defined in the following paragraph), H, F, Cl, Br, $CO_2H$, $CO_2(C_{1-6}$ alkyl), CN, $CF_3$, $CCl_3$, etc. Preferred blocking groups are electron-withdrawing groups.

Preferred blocking groups are of the formula: —O—X—Y or —OR$^3$ wherein: X is C(O), S(O) or SO$_2$; Y is C$_{1-12}$ alkyl, C$_{1-12}$ alkoxy, C$_{3-12}$ cycloalkyl, C$_{5-12}$ aryl or C$_{5-12}$ aryl-C$_{1-6}$ alkyl, each of which may optionally be substituted with 1, 2 or 3 groups independently selected from F, Cl, Br, CO$_2$H, CO$_2$ (C$_{1-6}$ alkyl), CN, CF$_3$ or CCl$_3$; or Y is NR$^1$R$^2$; R$^1$ and R$^2$ are independently selected from H, C$_{1-12}$ alkyl, C$_{3-12}$ cycloalkyl, C$_{5-12}$ aryl, C$_{5-12}$ aryl-C$_{1-6}$ alkyl; or R$^1$ and R$^2$ may be joined to form a C$_{3-12}$ saturated heterocyclic group; R$^3$ is C$_{1-12}$ alkyl or C$_{3-12}$ cycloalkyl, each of which may optionally be substituted with 1, 2 or 3 groups independently selected from F, Cl, Br, CO$_2$(C$_{1-6}$ alkyl), CN, CF$_3$ or CCl$_3$; or R$^3$ is C$_{1-12}$ aryl or C$_{5-12}$ aryl-C$_{1-6}$ alkyl, each of which may optionally be substituted with 1, 2, 3, 4 or 5 groups selected from F, Cl, Br, CO$_2$H, CO$_2$(C$_{1-6}$ alkyl), CN, CF$_3$ or CCl$_3$. When R$^3$ is C$_{1-12}$ alkyl or C$_{3-12}$ cycloalkyl, it is typically substituted with 1, 2 or 3 groups as defined above. When R$^1$ and R$^2$ are joined to form a C$_{3-12}$ saturated heterocyclic group, it is meant that R$^1$ and R$^2$ together with the nitrogen atom form a saturated heterocyclic group containing any number of carbon atoms between 3 and 12 (e.g. C$_3$, C$_4$, C$_5$, C$_6$, C$_7$, C$_8$, C$_9$, C$_{10}$, C$_{11}$, C$_{12}$). The heterocyclic group may contain 1 or 2 heteroatoms (such as N, O or S) other than the nitrogen atom. Examples of C$_{3-12}$ saturated heterocyclic groups are pyrrolidinyl, piperidinyl, morpholinyl, piperazinyl, imidazolidinyl, azetidinyl and aziridinyl.

Blocking groups —O—X—Y and —OR$^3$ can be prepared from —OH groups by standard derivatizing procedures, such as reaction of the hydroxyl group with an acyl halide, alkyl halide, sulfonyl halide, etc. Hence, the oxygen atom in —O—X—Y is preferably the oxygen atom of the hydroxyl group, while the —X—Y group in —O—X—Y preferably replaces the hydrogen atom of the hydroxyl group.

Alternatively, the blocking groups may be accessible via a substitution reaction, such as a Mitsonobu-type substitution. These and other methods of preparing blocking groups from hydroxyl groups are well known.

More preferably, the blocking group is —OC(O)CF$_3$ [137], or a carbamate group —OC(O)NR$^1$R$^2$, where R$^1$ and R$^2$ are independently selected from C$_{1-6}$ alkyl. More preferably, R$^1$ and R$^2$ are both methyl i.e. the blocking group is —OC(O)NMe$_2$. Carbamate blocking groups have a stabilizing effect on the glycosidic bond and may be prepared under mild conditions.

Preferred modified MenA saccharides contain n monosaccharide units, where at least h % of the monosaccharide units do not have —OH groups at both of positions 3 and 4. The value of h is 24 or more (e.g. 25, 26, 27, 28, 29, 30, 35, 40, 45, 50, 55, 60, 65, 70, 75, 80, 85, 90, 95, 98, 99 or 100) and is preferably 50 or more. The absent —OH groups are preferably blocking groups as defined above.

Other preferred modified MenA saccharides comprise monosaccharide units, wherein at least s of the monosaccharide units do not have —OH at the 3 position and do not have —OH at the 4 position. The value of s is at least 1 (e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90). The absent —OH groups are preferably blocking groups as defined above.

Suitable modified MenA saccharides for use with the invention have the formula:

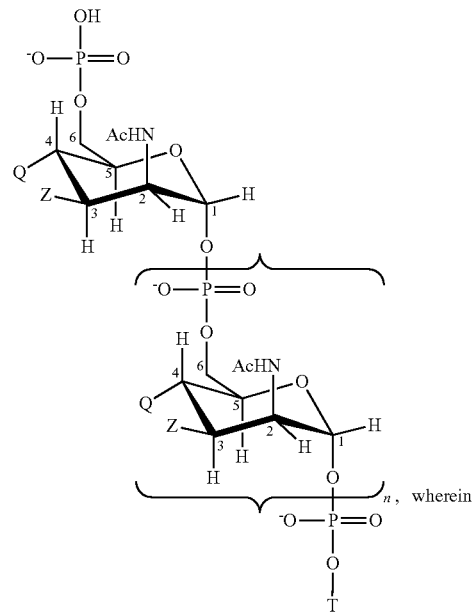

n is an integer from 1 to 100 (preferably an integer from 15 to 25);
T is of the formula (A) or (B):

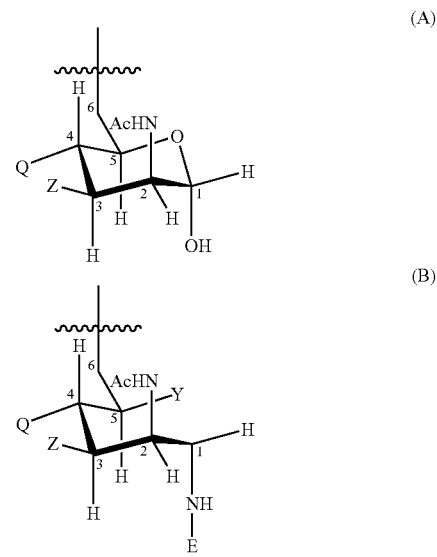

each Z group is independently selected from OH or a blocking group as defined above; and
each Q group is independently selected from OH or a blocking group as defined above;
Y is selected from OH or a blocking group as defined above;
E is H or a nitrogen protecting group;
and wherein more than about 7% (e.g. 8%, 9%, 10% or more) of the Q groups are blocking groups.

Each of the n+2 Z groups may be the same or different from each other. Likewise, each of the n+2 Q groups may be the same or different from each other. All the Z groups may be OH. Alternatively, at least 10%, 20, 30%, 40%, 50% or 60% of the Z groups may be OAc. Preferably, about 70% of the Z groups are OAc, with the remainder of the Z groups being OH or blocking groups as defined above. At least about 7% of Q groups are blocking groups. Preferably, at least 10%, 20%, 30%, 40%, 50%, 60%, 70%, 80%, 90% or even 100% of the Q groups are blocking groups.

Preferred compositions of the invention can be stored for 28 days at 37° C. and, after that period, less than f % of the initial total amount of conjugated MenA saccharide will be unconjugated, where f is 20, 19, 18, 17, 16, 15, 14, 13, 12, 11, 10, 9, 8, 7, 6, 5 or lower.

Meningococcal capsular polysaccharides are typically prepared by a process comprising the steps of polysaccharide precipitation (e.g. using a cationic detergent), ethanol fractionation, cold phenol extraction (to remove protein) and ultracentrifugation (to remove LPS) [e.g. ref. 138]. A more preferred process [108], however, involves polysaccharide precipitation followed by solubilisation of the precipitated polysaccharide using a lower alcohol. Precipitation can be achieved using a cationic detergent such as tetrabutylammonium and cetyltrimethylammonium salts (e.g. the bromide salts), or hexadimethrine bromide and myristyltrimethylammonium salts. Cetyltrimethylammonium bromide ('CTAB') is particularly preferred [139]. Solubilisation of the precipitated material can be achieved using a lower alcohol such as methanol, propan-1-ol, propan-2-ol, butan-1-ol, butan-2-ol, 2-methyl-propan-1-ol, 2-methyl-propan-2-ol, diols, etc., but ethanol is particularly suitable for solubilising CTAB-polysaccharide complexes. Ethanol is preferably added to the precipitated polysaccharide to give a final concentration (based on total content of ethanol and water) of between 50% and 95%.

After re-solubilisation, the polysaccharide may be further treated to remove contaminants. This is particularly important in situations where even minor contamination is not acceptable (e.g. for human vaccine production). This will typically involve one or more steps of filtration e.g. depth filtration, filtration through activated carbon may be used, size filtration and/or ultrafiltration. Once filtered to remove contaminants, the polysaccharide may be precipitated for further treatment and/or processing. This can be conveniently achieved by exchanging cations (e.g. by the addition of calcium or sodium salts).

As an alternative to purification, capsular saccharides of the present invention may be obtained by total or partial synthesis e.g. Hib synthesis is disclosed in ref. 140, and MenA synthesis in ref. 141.

Compositions of the invention comprise capsular saccharides from at least two serogroups of N. meningitidis. The saccharides are preferably prepared separately (including any fragmentation, conjugation, modification, etc.) and then admixed to give a composition of the invention.

Where the composition comprises capsular saccharide from serogroup A, however, it is preferred that the serogroup A saccharide is not combined with the other saccharide(s) until shortly before use, in order to minimise the potential for hydrolysis. This can conveniently be achieved by having the serogroup A component (typically together with appropriate excipients) in lyophilised form and the other serogroup component(s) in liquid form (also with appropriate excipients), with the liquid components being used to reconstitute the lyophilised MenA component when ready for use. Where an aluminium salt adjuvant is used, it is preferred to include the adjuvant in the vial containing the with the liquid vaccine, and to lyophilise the MenA component without adjuvant.

A composition of the invention may thus be prepared from a kit comprising: (a) capsular saccharide from N. meningitidis serogroup A, in lyophilised form; and (b) the further antigens from the composition, in liquid form. The invention also provides a method for preparing a composition of the invention, comprising mixing a lyophilised capsular saccharide from N. meningitidis serogroup A with the further antigens, wherein said further antigens are in liquid form.

The invention also provides a kit comprising: (a) a first container containing capsular saccharides from two or more of N. meningitidis serogroups C, W135 and Y, all in lyophilised form; and (b) a second container containing in liquid form (i) a composition which, after administration to a subject, is able to induce an antibody response in that subject, wherein the antibody response is bactericidal against two or more (e.g. 2 or 3) of hypervirulent lineages A4, ET-5 and lineage 3 of N. meningitidis serogroup B, (ii) capsular saccharides from none or one of N. meningitidis serogroups C, W135 and Y, and optionally (iii) further antigens (see below) that do not include meningococcal capsular saccharides, wherein, reconstitution of the contents of container (a) by the contents of container (b) provides a composition of the invention.

Within each dose, the amount of an individual saccharide antigen will generally be between 1-50 μg (measured as mass of saccharide), with about 2.5 μg, 5 μg or 10 μg of each being preferred. With A:C:W135:Y weight ratios of 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1, therefore, the amount represented by the FIG. 1 is preferably about 2.5 kg, 5 μg or 10 μg. For a 1:1:1:1 ratio A:C:W:Y composition and a 10 μg per saccharide, therefore, 40 μg saccharide is administered per dose. Preferred compositions have about the following μg saccharide per dose:

| A    | 10 | 0  | 0 | 0   | 10 | 5 | 2.5 |
| C    | 10 | 10 | 5 | 2.5 | 5  | 5 | 2.5 |
| W135 | 10 | 10 | 5 | 2.5 | 5  | 5 | 2.5 |
| Y    | 10 | 10 | 5 | 2.5 | 5  | 5 | 2.5 |

Preferred compositions of the invention comprise less than 50 μg meningococcal saccharide per dose. Other preferred compositions comprise ≤40 μg meningococcal saccharide per dose. Other preferred compositions comprise ≤30 μg meningococcal saccharide per dose. Other preferred compositions comprise ≤25 μg meningococcal saccharide per dose. Other preferred compositions comprise ≤20 μg meningococcal saccharide per dose. Other preferred compositions comprise ≤10 μg meningococcal saccharide per dose but, ideally, compositions of the invention comprise at least 10 μg meningococcal saccharide per dose.

The Menjugate™ and NeisVac™ MenC conjugates use a hydroxide adjuvant, whereas Meningitec™ uses a phosphate. It is possible in compositions of the invention to adsorb some antigens to an aluminium hydroxide but to have other antigens in association with an aluminium phosphate. For tetravalent serogroup combinations, for example, the following permutations are available:

| Serogroup | Aluminium salt (H = a hydroxide; P = a phosphate) | | | | | | | | | | | | | | | |
|---|---|---|---|---|---|---|---|---|---|---|---|---|---|---|---|---|
| A | P | H | P | H | H | H | P | P | P | H | H | H | P | P | P | H |
| C | P | H | H | P | H | H | P | H | P | P | H | P | H | P | P | P |
| W135 | P | H | H | H | P | H | H | P | H | H | P | P | P | P | H | P |
| Y | P | H | H | H | H | P | H | H | P | P | H | P | H | P | P | P |

For trivalent *N. meningitidis* serogroup combinations, the following permutations are available:

| Serogroup | Aluminium salt (H = a hydroxide; P = a phosphate) | | | | | | | |
|---|---|---|---|---|---|---|---|---|
| C | P | H | H | H | P | P | P | H |
| W135 | P | H | H | P | H | P | H | P |
| Y | P | H | P | H | H | H | P | P |

*Haemophilus influenzae* Type B

Where the composition includes a *H. influenzae* type B antigen, it will typically be a Hib capsular saccharide antigen. Saccharide antigens from *H. influenzae* b are well known.

Advantageously, the Hib saccharide is covalently conjugated to a carrier protein, in order to enhance its immunogenicity, especially in children. The preparation of polysaccharide conjugates in general, and of the Hib capsular polysaccharide in particular, is well documented [e.g. references 142 to 150 etc.]. The invention may use any suitable Hib conjugate. Suitable carrier proteins are described below, and preferred carriers for Hib saccharides are $CRM_{197}$ ('HbOC'), tetanus toxoid ('PRP-T') and the outer membrane complex of *N. meningitidis* ('PRP-OMP').

The saccharide moiety of the conjugate may be a polysaccharide (e.g. full-length polyribosylribitol phosphate (PRP)), but it is preferred to hydrolyse polysaccharides to form oligosaccharides (e.g. MW from ~1 to ~5 kDa).

A preferred conjugate comprises a Hib oligosaccharide covalently linked to $CRM_{197}$ via an adipic acid linker [151, 152]. Tetanus toxoid is also a preferred carrier.

Administration of the Hib antigen preferably results in an anti-PRP antibody concentration of ≥0.15 µg/ml, and more preferably ≥1 µg/ml.

Compositions of the invention may comprise more than one Hib antigen.

Where a composition includes a Hib saccharide antigen, it is preferred that it does not also include an aluminium hydroxide adjuvant. If the composition includes an aluminium phosphate adjuvant then the Hib antigen may be adsorbed to the adjuvant [153] or it may be non-adsorbed [154].

Hib antigens may be lyophilised e.g. together with meningococcal antigens.

*Streptococcus pneumoniae*

Where the composition includes a *S. pneumoniae* antigen, it will typically be a capsular saccharide antigen which is preferably conjugated to a carrier protein [e.g. refs. 155 to 157]. It is preferred to include saccharides from more than one serotype of *S. pneumoniae*. For example, mixtures of polysaccharides from 23 different serotype are widely used, as are conjugate vaccines with polysaccharides from between 5 and 11 different serotypes [158]. For example, PrevNar™ [159] contains antigens from seven serotypes (4, 6B, 9V, 14, 18C, 19F, and 23F) with each saccharide individually conjugated to $CRM_{197}$ by reductive amination, with 2 µg of each saccharide per 0.5 ml dose (4 kg of serotype 6B), and with conjugates adsorbed on an aluminium phosphate adjuvant. Compositions of the invention preferably include at least serotypes 6B, 14, 19F and 23F. Conjugates may be adsorbed onto an aluminium phosphate.

As an alternative to using saccharide antigens from pneumococcus, the composition may include one or more polypeptide antigens. Genome sequences for several strains of pneumococcus are available [160,161] and can be subjected to reverse vaccinology [162-165] to identify suitable polypeptide antigens [166,167]. For example, the composition may include one or more of the following antigens: PhtA, PhtD, PhtB, PhtE, SpsA, LytB, LytC, LytA, Sp125, Sp101, Sp128, Sp130 and Sp130, as defined in reference 168. The composition may include more than one (e.g. 2, 3, 4, 5, 6, 7, 8, 9 10, 11, 12, 13 or 14) of these antigens.

In some embodiments, the composition may include both saccharide and polypeptide antigens from pneumococcus. These may be used in simple admixture, or the pneumococcal saccharide antigen may be conjugated to a pneumococcal protein. Suitable carrier proteins for such embodiments include the antigens listed in the previous paragraph [168].

Pneumococcal antigens may be lyophilised e.g. together with meningococcal and/or Hib antigens.

Covalent Conjugation

Capsular saccharides in compositions of the invention will usually be conjugated to carrier protein(s). In general, conjugation enhances the immunogenicity of saccharides as it converts them from T-independent antigens to T-dependent antigens, thus allowing priming for immunological memory. Conjugation is particularly useful for paediatric vaccines and is a well known technique [e.g. reviewed in refs. 169 and 142-150].

Preferred carrier proteins are bacterial toxins or toxoids, such as diphtheria toxoid or tetanus toxoid. The $CRM_{197}$ diphtheria toxoid [170-172] is particularly preferred. Other suitable carrier proteins include the *N. meningitidis* outer membrane protein [173], synthetic peptides [174,175], heat shock proteins [176,177], pertussis proteins [178,179], cytokines [180], lymphokines [180], hormones [180], growth factors [180], artificial proteins comprising multiple human $CD4^+$ T cell epitopes from various pathogen-derived antigens [181], protein D from *H. influenzae* [182,183], pneumococcal surface protein PspA [184], iron-uptake proteins [185], toxin A or B from *C. difficile* [186], etc. Preferred carriers are diphtheria toxoid, tetanus toxoid, *H. influenzae* protein D, and $CRM_{197}$.

Within a composition of the invention, it is possible to use more than one carrier protein e.g. to reduce the risk of carrier suppression. Thus different carrier proteins can be used for different serogroups e.g. serogroup A saccharides might be conjugated to $CRM_{197}$ while serogroup C saccharides might be conjugated to tetanus toxoid. It is also possible to use more than one carrier protein for a particular saccharide antigen e.g. serogroup A saccharides might be in two groups, with some conjugated to CRM$_{197}$ and others conjugated to tetanus toxoid. In general, however, it is preferred to use the same carrier protein for all saccharides.

A single carrier protein might carry more than one saccharide antigen [187]. For example, a single carrier protein might have conjugated to it saccharides from serogroups A and C. To achieve this goal, saccharides can be mixed prior to the conjugation reaction. In general, however, it is preferred to have separate conjugates for each serogroup.

Conjugates with a saccharide:protein ratio (w/w) of between 1:5 (i.e. excess protein) and 5:1 (i.e. excess saccharide) are preferred. Ratios between 1:2 and 5:1 are preferred, as are ratios between 1:1.25 and 1:2.5 are more preferred. Excess carrier protein may be preferred for MenA and MenC.

Conjugates may be used in conjunction with free carrier protein [188]. When a given carrier protein is present in both free and conjugated form in a composition of the invention, the unconjugated form is preferably no more than 5% of the total amount of the carrier protein in the composition as a whole, and more preferably present at less than 2% by weight.

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [189,190, etc.]). Other suitable techniques use carbodiimides, hydrazides, active esters, norborane, p-nitrobenzoic acid, N-hydroxysuccinimide, S-NHS, EDC, TSTU; see also the introduction to reference 148).

Linkages via a linker group may be made using any known procedure, for example, the procedures described in references 191 and 192. One type of linkage involves reductive amination of the polysaccharide, coupling the resulting amino group with one end of an adipic acid linker group, and then coupling a protein to the other end of the adipic acid linker group [146,193,194]. Other linkers include B-propionamido [195], nitrophenyl-ethylamine [196], haloacyl halides [197], glycosidic linkages [198], 6-aminocaproic acid [199], ADH [200], $C_4$ to $C_{12}$ moieties [201] etc. As an alternative to using a linker, direct linkage can be used. Direct linkages to the protein may comprise oxidation of the polysaccharide followed by reductive amination with the protein, as described in, for example, references 202 and 203.

A process involving the introduction of amino groups into the saccharide (e.g. by replacing terminal =O groups with —NH$_2$) followed by derivatisation with an adipic diester (e.g. adipic acid N-hydroxysuccinimido diester) and reaction with carrier protein is preferred. Another preferred reaction uses CDAP activation with a protein D carrier e.g. for MenA or MenC.

After conjugation, free and conjugated saccharides can be separated. There are many suitable methods, including hydrophobic chromatography, tangential ultrafiltration, diafiltration etc. [see also refs. 204 & 205, etc.].

Where the composition of the invention includes a conjugated oligosaccharide, it is preferred that oligosaccharide preparation precedes conjugation.

Further and Alternative Serogroup B Polypeptide Antigens

The invention provides a composition which, after administration to a subject, is able to induce an antibody response in that subject, wherein the antibody response is bactericidal against two or three of hypervirulent lineages A4, ET-5 and lineage 3 of *N. meningitidis* serogroup B.

Although NadA, 741, 936, 953 and 287 are preferred antigens for achieving this broad protection, other MenB polypeptide antigens which may be included in compositions of the invention (optionally in combination with one or more of the five basic antigens) include those comprising one of the following amino acid sequences: SEQ ID NO:650 from ref. 8; SEQ ID NO:878 from ref. 8; SEQ ID NO:884 from ref. 8; SEQ ID NO:4 from ref. 9; SEQ ID NO:598 from ref. 10; SEQ ID NO:818 from ref. 10; SEQ ID NO:864 from ref. 10; SEQ ID NO:866 from ref. 10; SEQ ID NO:1196 from ref. 10; SEQ ID NO:1272 from ref. 10; SEQ ID NO:1274 from ref. 10; SEQ ID NO:1640 from ref. 10; SEQ ID NO:1788 from ref. 10; SEQ ID NO:2288 from ref. 10; SEQ ID NO:2466 from ref. 10; SEQ ID NO:2554 from ref. 10; SEQ ID NO:2576 from ref 10; SEQ ID NO:2606 from ref 10; SEQ ID NO:2608 from ref. 10; SEQ ID NO:2616 from ref. 10; SEQ ID NO:2668 from ref. 10; SEQ ID NO:2780 from ref 10; SEQ ID NO:2932 from ref. 10; SEQ ID NO:2958 from ref. 10; SEQ ID NO:2970 from ref. 10; SEQ ID NO:2988 from ref. 10, or a polypeptide comprising an amino acid sequence which: (a) has 50% or more identity (e.g. 60%, 70%, 80%, 90%, 95%, 99% or more) to said sequences; and/or (b) comprises a fragment of at least n consecutive amino acids from said sequences, wherein n is 7 or more (eg. 8, 10, 12, 14, 16, 18, 20, 25, 30, 35, 40, 50, 60, 70, 80, 90, 100, 150, 200, 250 or more). Preferred fragments for (b) comprise an epitope from the relevant sequence. More than one (e.g. 2, 3, 4, 5, 6) of these polypeptides may be included.

General

The term "comprising" means "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 206. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is taught in reference 207.

The term "alkyl" refers to alkyl groups in both straight and branched forms, The alkyl group may be interrupted with 1, 2 or 3 heteroatoms selected from —O—, —NH— or —S—. The alkyl group may also be interrupted with 1, 2 or 3 double and/or triple bonds. However, the term "alkyl" usually refers to alkyl groups having no heteroatom interruptions or double or triple bond interruptions. Where reference is made to $C_{1-12}$ alkyl, it is meant the alkyl group may contain any number of carbon atoms between 1 and 12 (e.g. $C_1$, $C_2$, $C_3$, $C_4$, $C_5$, $C_6$, $C_7$, $C_8$, $C_9$, $C_{10}$, $C_{11}$, $C_{12}$). Similarly, where reference is made to $C_{1-6}$ alkyl, it is meant the alkyl group may contain any number of carbon atoms between 1 and 6 (e.g. $C_1$, $C_2$, $C_3$, $C_4$, $C_5$, $C_6$).

The term "cycloalkyl" includes cycloalkyl, polycycloalkyl, and cycloalkenyl groups, as well as combinations of these with alkyl groups, such as cycloalkylalkyl groups. The cycloalkyl group may be interrupted with 1, 2 or 3 heteroatoms selected from —O—, —NH— or —S—. However, the term "cycloalkyl" usually refers to cycloalkyl groups having no heteroatom interruptions Examples of cycloalkyl groups include cyclopentyl, cyclohexyl, cyclohexenyl, cyclohexylmethyl and adamantyl groups. Where reference is made to $C_{3-12}$ cycloalkyl, it is meant that the cycloalkyl group may contain any number of carbon atoms between 3 and 12 (e.g. $C_3$, $C_4$, $C_5$, $C_6$, $C_7$, $C_8$, $C_9$, $C_{10}$, $C_{11}$, $C_{12}$).

The term "aryl" refers to an aromatic group, such as phenyl or naphthyl. Where reference is made to $C_{5-12}$ aryl, it is meant that the aryl group may contain any number of carbon atoms between 5 and 12 (e.g. $C_5$, $C_6$, $C_7$, $C_8$, $C_9$, $C_{10}$, $C_{11}$, $C_{12}$).

The term "$C_{5-12}$ aryl-$C_{1-6}$ alkyl" refers to groups such as benzyl, phenylethyl and naphthylmethyl.

Nitrogen protecting groups include silyl groups (such as TMS, TES, TBS, TIPS), acyl derivatives (such as phthalimides, trifluoroacetamides, methoxycarbonyl, ethoxycarbonyl, t-butoxycarbonyl (Boc), benzyloxycarbonyl (Z or Cbz), 9-fluorenylmethoxycarbonyl (Fmoc), 2-(trimethylsilyl) ethoxy carbonyl, 2,2,2-trichloroethoxycarbonyl (Troc)), sulfonyl derivatives (such as β-trimethylsilylethanesulfonyl (SES)), sulfenyl derivatives, $C_{1-12}$ alkyl, benzyl, benzhydryl, trityl, 9-phenylfluorenyl etc. A preferred nitrogen protecting group is Fmoc.

Sequences included to facilitate cloning or purification, etc., do not necessarily contribute to the invention and may be omitted or removed.

It will be appreciated that sugar rings can exist in open and closed form and that, whilst closed forms are shown in structural formulae herein, open forms are also encompassed by the invention.

MODES FOR CARRYING OUT THE INVENTION

ΔG287-953 Hybrid Protein

DNA encoding protein 287 from meningococcal serogroup B strain 394/98 and protein 953 from meningococcal serogroup B strain 2996 were digested and ligated, together with a short linker sequence, to give a plasmid encoding amino acid sequence SEQ ID 7. The plasmid was transfected into *E. coli* and bacteria were grown to express the protein.

After adequate growth, bacteria were harvested and the protein was purified. From culture, bacteria were centrifuged and the pellet was homogenized in the presence of 50 mM acetate buffer (H 5) with a pellet:buffer volume ratio of 1:8. Lysis was performed using a high pressure homogenizer (AVESTIN, 4 cycles at 14000 psi). After lysis, urea was added at final concentration of 5M, followed by agitation for 1 hour at room temperature. The pH was reduced from 6 to 5 using 200 mM acetate buffer (pH 4)+5 M urea. The mixture was centrifuged at 16800 g for 60 minutes at 2-8° C. The supernatant was collected and filtered by SARTOBRAN P (0.45-0.22 μm SARTORIUS).

Protein in the filtered supernatant was stable for ≥30 days at −20° C. and for ≥15 days at 2-8° C.

Protein was further purified on a cationic exchange column (SPFF, Amersham Biosciences) with elution using 350 mM NaCl+50 mM acetate+5 M urea pH 5.00. The majority of impurities were present in the flow-thru. A pre-elution washing using a lower NaCl concentration (180 mM) advantageously eliminated two contaminating *E. coli* proteins.

The eluted material was adjusted to pH 8 (using 200 mM TRIS/HCl+5 M urea pH 9) and further purified on a Q Sepharose HP column (Amersham) with elution using 150 mM NaCl+20 mM TRIS/HCl pH 8.00 in 5 M urea. Again, a pre-elution washing with reduced salt (90 mM) was useful for eliminating impurities.

The filtered eluted material from Q HP column was diluted 1:2 using PBS pH 7.00 (150 mM NaCl+10 mM potassium phosphate, pH 7.00) and then diafiltered against 10 volumes of PBS pH 7.00 by tangential ultrafiltration. At the end of diafiltration the material was concentrated 1.6 times to about 1.2 mg/ml total proteins. Using a 30,000 Da cut-off membrane Regenerated Cellulose membrane 50 cm$^2$, Millipore PLCTK 30) it was possible to dialyze the material with a yield of about 90%.

936-ΔG741 Hybrid Protein

DNA encoding protein 936 from meningococcal serogroup B strain 2996 and protein 741 from meningococcal serogroup B strain MC58 were digested and ligated, together with a short linker sequence, to give a plasmid encoding amino acid sequence SEQ ID 8. The plasmid was transfected into *E. coli* and bacteria were grown to express the protein. The recombinant protein was not secreted, but remained soluble within the bacteria.

After adequate growth, bacteria were centrifuged to give a humid paste and treated as follows:

Homogenisation by high pressure system in presence of 20 mM sodium phosphate pH 7.00.

Centrifugation and clarification by orthogonal filtration.

Cationic column chromatography (SP Sepharose Fast Flow), with elution by 150 mM NaCl in 20 mM sodium phosphate pH 7.00.

Anionic column chromatography (Q Sepharose XL) with flow-through harvesting.

Hydrophobic column chromatography (Phenyl Sepharose 6 Fast Flow High Sub) with elution by 20 mM sodium phosphate, pH 7.00.

Diafiltration against PBS pH 7.4 with a 10 Kd cut-off.

Final sterile filtration and storing at −20° C.

Protein in the final material was stable for at least 3 months both at −20° C. and at 2-8° C.

NadA$^{(NL)(C)}$ Protein

DNA encoding NadA protein from meningococcal serogroup B strain 2996 was digested to remove the sequence encoding its C-terminus, to give a plasmid encoding amino acid sequence SEQ ID 1. The plasmid was transfected into *E. coli* and bacteria were grown to express the protein. The recombinant protein was secreted into the culture medium, and the leader peptide was absent in the secreted protein (SEQ ID 2). The supernatant was treated as follows:

Concentration 7× and diafiltration against buffer 20 mM TRIS/HCl pH7.6 by cross flow UF (Cut off 30 Kd).
Anionic column chromatography (Q Sepharose XL), with elution by 400 mM NaCl in 20 mM TRIS/HCl pH 7.6.
Hydrophobic column chromatography step (Phenyl Sepharose 6 Fast Flow High Sub), with elution by 50 mM NaCl in TRIS/HCl pH 7.6.
Hydroxylapatite ceramic column chromatography (HA Macro. Prep) with elution by 200 mM sodium phosphate pH 7.4.
Diafiltration (cut off 30 Kd) against PBS pH 7.4
Final sterile filtration and storing at −20° C.

Protein in the final material was stable for at least 6 months both at −20° C. and at 2-8° C.

NadA protein is susceptible to degradation, and truncated forms of NadA may be detected by western blot or by mass spectrometry (e.g. by MALDI-TOF) indicating up to 10 kDa MW loss. Degradation products can be separated from native NadA by gel filtration (e.g. using column TSK 300SWXL, precolumn TSKSWXL, TOSOHAAS). Such filtration gives three peaks: (i) a first peak with retention time 12.637 min and apparent MW 885.036 Da; (ii) retention time 13.871 min and apparent MW 530.388 Da; (iii) retention time 13.871 min and apparent MW 530.388 Da. Light scattering analysis of the three peaks reveals real MW values of (i) 208500 Da, (ii) 98460 Da, (iii) 78760 Da. Thus the first peak contains NadA aggregates, and the third peak contains degradation products.

As the predicted molecular weight of NadA$^{(NL)(C)}$ is 34.113 Da, peak (ii) contains a trimeric protein, which is the desired antigen.

Antigenic Combinations

Mice were immunised with a composition comprising the three proteins and an aluminium hydroxide adjuvant. For comparison purposes, the three proteins were also tested singly. Ten mice were used per group. The mixture was able to induce high bactericidal titres against various strains:

Combination and Comparison with OMVs

In further experiments, the adjuvanted antigens (20 μg of each antigen per dose) were administered in combination with 10 μg OMVs prepared either from strain H44/76 (Norway) or strain 394/98 (New Zealand). Positive controls were the anti-capsular SEAM-3 mAb for serogroup B or CRM197-conjugated capsular saccharides for other strains. Results (bactericidal titres) are shown in Table 1. The mixture almost always gives better titres than simple OMVs and, furthermore, the addition of the mixture to OMVs almost always significantly enhances the efficacy of the OMVs. Moreover, in many cases the antigen mixture matches or exceeds the response seen with the positive control.

Hypervirulent Lineage Tests

The following antigens were tested against a variety of serogroup B strains from a variety of hypervirulent lineages:
(a) NadA$^{(NL)(C)}$
(b) ΔG287-953
(c) 936-ΔG741
(d) a mixture of (a), (b) and (c)
(e) OMVs prepared from strain H44/76 (Norway)
(f) OMVs prepared from strain 394/98 (New Zealand)
(g) A mixture of ΔG287 and (e)
(h) A mixture of (d) and (e)
(i) A mixture of (d) and (f)

SEAM-3 was used as a positive control.

Results were as follows, expressed as the percentage of strains in the indicated hypervirulent lineage where the serum bactericidal titre exceeded 1024:

|  | # strains | (a) | (b) | (c) | (d) | (e) | (f) | (g) | (h) | (i) | S-3 |
|---|---|---|---|---|---|---|---|---|---|---|---|
| A4 | 4 | 50 | 50 | 0 | 100 | 25 | 25 | 25 | 100 | 100 | + |
| ET-5 | 8 | 25 | 75 | 88 | 100 | 71 | 14 | 71 | 100 | 100 | + |
| Lineage 3 | 13 | 0 | 75 | 15 | 93 | 8 | 85 | 8 | 92 | 93 | + |
| ET-37 | 4 | 11 | 22 | 0 | 33 | 0 | 0 | 0 | 22 | 25 | + |

| | Meningococcal strain (Serogroup) | | | | | | | |
|---|---|---|---|---|---|---|---|---|
| | 2996 (B) | MC58 (B) | NGH38 | 394/98 (B) | H44/76 (B) | F6124 (A) | BZ133 (C) | C11 (C) |
| (1) | 32000 | 16000 | 130000 | 16000 | 32000 | 8000 | 16000 | 8000 |
| (2) | 256 | 131000 | 128 | 16000 | 32000 | 8000 | 16000 | <4 |
| (3) | 32000 | 8000 | — | — | — | 8000 | — | 32000 |
| Mix | 32000 | 32000 | 65000 | 16000 | 260000 | 65000 | >65000 | 8000 |

'—' indicates that this strain contains no NadA gene

Looking at individual mice, the triple mixture induced high and consistent bactericidal titres against the three serogroup B strains from which the individual antigens are derived:

| | # | | | | | | | | | |
|---|---|---|---|---|---|---|---|---|---|---|
| | 1 | 2 | 3 | 4 | 5 | 6 | 7 | 8 | 9 | 10 |
| 2996 | 32768 | 16384 | 65536 | 32768 | 32768 | 65536 | 65536 | 32768 | 65536 | 8192 |
| MC58 | 65536 | 32768 | 65536 | 65536 | 65536 | 8192 | 65536 | 32768 | 32768 | 65536 |
| 394/98 | 65536 | 4096 | 16384 | 4096 | 8192 | 4096 | 32768 | 16384 | 8192 | 16384 |

Against particular reference strains, bactericidal titres were as follows:

| Strain | | (a) | (b) | (c) | (d) | (e) | (f) | (g) | (h) | (i) | S-3 |
|---|---|---|---|---|---|---|---|---|---|---|---|
| A4 | 961-5945 | 128 | 2048 | <8 | 2048 | 262144 | 8192 | 262144 | 262144 | 4096 | 8192 |
| ET-5 | 44/76 | <4 | 2048 | 32768 | 131072 | 524288 | 8192 | 524288 | 524288 | 524288 | 16384 |
| Lineage 3 | 394/98 | <4 | 1024 | 32 | 4096 | <4 | 16384 | 256 | 16384 | 16384 | 16384 |
| ET-37 | LPN17592 | 2048 | 1024 | 256 | 4096 | <8 | <8 | 512 | 16384 | 65536 | 1024 |

Compositions (d), (h) and (i) therefore induce bactericidal antibody responses against a wide variety of strains of serogroup B meningococcus from within hypervirulent lineages A4, ET-5 and lineage 3. Titres using compositions h) and (i) were generally higher than with (d), but the coverage of strains within hypervirulent lineages A4, ET-5 and lineage 3 were no better.

Coverage of untyped strains was also high with compositions (d), (h) and (i).

Analysis of NadA N-Terminus Domain

Purified *N. meningitidis* NadA protein is known to bind to human epithelial cells [17] (e.g. Chang cells, HeLa cells, Hep-2 cells), and recombinant *E. coli* which express NadA display an adherent phenotype [18]. These *E. coli* are also able to invade epithelial cells, and intracellular NadA$^{+ve}$ *E. coli* can be detected in Chang cells by immunofluorescence (after membrane permeabilisation) and by electron microscopy. NadA is thus believed function as an adhesin and an invasin for epithelial cells.

On the basis of secondary structure analysis, mature NadA has been subdivided into three putative domains: a N-terminal globular domain (aa 24-87), an α-helix internal region (aa 88-350) with high coiled-coil propensity, and a C-terminal membrane anchor (aa 351-405). The role of the N-terminal globular domain in host-cell interaction was investigated.

A truncated nadA gene coding for a protein devoid of amino acids 30-87 was cloned into pET-21 vector (pET-NadAΔ30-87) and expressed in *E. coli* BL21(DE3) strain. Amino acids 24-29 were retained to allow processing of the leader peptide and correct maturation of the protein. Western blot and FACS analysis confirmed that NadAΔ30-87 was expressed and formed oligomers on the *E. coli* cell surface i.e. deletion of the N-terminal domain does not interfere with the expression, export and membrane localization of NadA. However, the recombinant *E. coli* strain completely lost the capacity to adhere to Chang epithelial cells. The N-terminus domain is thus implicated in adhesin activity.

To further investigate which part of the N-terminal domain is involved in the interaction, the region was additionally divided into three putative sub-domains: amino acids 24-42, containing a predicted α-helix region with hydrophobic residues; amino acids 43-70, the internal part without a predicted defined secondary structure; and amino acids 71-87 containing an other predicted α-helix structure. Three constructs, each encoding a protein deleted of a single sub-domain, were generated and then introduced into *E. coli* BL21(DE3), obtaining the following strains: BL21(DE3)/pET-NadAΔΔ24-42, BL21(DE3)/pET-NadAΔΔ43-70 and BL21 (DE3)/pET-NadAΔΔ71-87. Surface localisation of the oligomers was confirmed by western blot and FACS analysis, but adhesion to Chang epithelial cells was no better than the control BL21(DE3)/pET *E. coli* strain. These results, confirmed also using immunofluorescence microscopy analysis, indicate that the entire globular N-terminal domain of NadA is important in the interaction with human cells.

Combination with Meningococcal and/or Hib Conjugates

The triple MenB composition is combined with a mixture of oligosaccharide conjugates for serogroups C, W135 and Y, to give a vaccine containing the following antigens:

| Component | Quantity per 0.5 ml dose |
|---|---|
| Serogroup C conjugate | 10 μg saccharide + 12.5-25 μg CRM$_{197}$ |
| Serogroup W135 conjugate | 10 μg saccharide + 6.6-20 μg CRM$_{197}$ |
| Serogroup Y conjugate | 10 μg saccharide + 6.6-20 μg CRM$_{197}$ |
| ΔG287-953 | 20 μg polypeptide |
| 936-ΔG741 | 20 μg polypeptide |
| NadA | 20 μg polypeptide |

A similar vaccine is prepared, including MenA conjugate (10 μg saccharide+12.5-33 μg CRM$_{197}$) and/or a HbOC Hib conjugate (10 μg saccharide+2-5 μg CRM$_{197}$).

Use of Modified MenA Saccharide

Capsular polysaccharide was purified from MenA and was hydrolysed to give MenA oligosaccharide. The polysaccharide (2 g) was hydrolyzed at 50° C. in 50 mM sodium acetate buffer, pH 4.75, at a polysaccharide concentration of 10 mg/mL for about 4 hours [135]. After hydrolysis, the solution was dried by rotary evaporation.

The oligosaccharide was activated using the following reaction scheme:

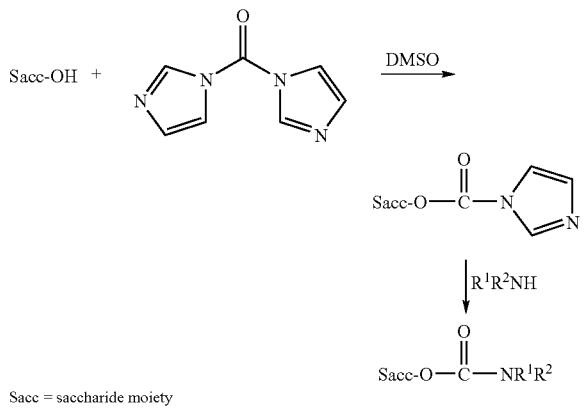

Sacc = saccharide moiety

The oligosaccharide was dissolved in DMSO to give a saccharide concentration of 10 mg/mL. According to a molar ratio of oligosaccharide:CDI being 1:20, 21.262 g of CDI was then added and the reaction mixture stirred for 16 hours at room temperature. The resulting MenA-CDI compound was purified by selective precipitation in a 80:20 (v/v) acetone: DMSO mixture followed by centrifugation. The efficiency of the activation reaction was calculated to be about 67.9% by determining the ratio of free imidazole to bonded imidazole.

In the second reaction step, the MenA-CDI oligosaccharide was solubilised in DMSO at a saccharide concentration of about 10 mg/mL. According to a molar ratio of MenA-CDI unit:DMA being 1:100, 36.288 g of 99% dimethylamine hydrochloride (i.e. $R^1$ & $R^2$=Me) was added and the reaction mixture stirred for 16 hours at room temperature. The reaction product was freeze-dried and re-solubilised in 10 mg/mL water solution.

To remove the low molecular weight reaction reagent (in particular the dimethylamine (DMA)) from the oligosaccharide preparation, a dialysis step was performed through a 3.5 kDa MWCO membrane (Spectra/Por™). Four dialysis steps were carried out: (i) 16 hours against 2 L of 1 M sodium chloride (dialysis factor 1:20), (ii) 16 hours against 2 L of 0.5 M sodium chloride (dialysis factor 1:20), (iii) and (iv) 16 hours against 2 L of WFI (dialysis factor 1:20). To improve the purification a diafiltration step was also performed through a 1 kDa MWCO membrane (Centricon™).

The purified MenA-CDI-DMA product was buffered at pH 6.5 in 25 mM L-histidine (Fluka™).

For preparing conjugates of the modified MenA saccharide (MenA-CDI-DMA), the overall process was as follows:

- hydrolysis of the polysaccharide to give oligosaccharide fragments
- sizing of the oligosaccharide fragments
- reductive amination of terminal aldehyde groups on the sized oligosaccharides
- protection of terminal —$NH_2$ groups by Fmoc group before the CDI reaction
- intrinsic de-protection of —$NH_2$ groups during the DMA reaction
- activation of terminal —$NH_2$ groups by SIDEA (N-hydroxysuccinimide adipic acid)
- covalent attachment to $CRM_{197}$ protein The modified MenA oligosaccharide conjugate is much more resistant to hydrolysis than its natural counterpart at elevated temperatures. After 28 days at 37° C., for instance, the percentage of released saccharide is 6.4% for the modified oligosaccharide vs. 23.5% for the natural antigen. Moreover, the titres induced by the modified oligosaccharides are not significantly lower than those obtained using the native sugar structures.

The modified MenA conjugate is combined with MenC, MenW135 and MenY conjugates as a substitute for the conjugate of unmodified oligosaccharide. This tetravalent mixture is mixed with the three MenB polypeptides to give a vaccine effective against serogroups A, B, C, W135 and Y of *N. meningitidis* in a single dose.

Pneumococcal Combinations

The three combined MenB proteins are mixed with pneumococcal saccharide conjugates to give a final concentration of 2 μg/dose of each of the pneumococcal serotypes (double for serotype 6B). The reconstituted vaccine thus contains the following antigens:

| Component | Quantity per 0.5 ml dose |
|---|---|
| Serogroup A conjugate | 5 μg saccharide + 6.25-16.5 μg $CRM_{197}$ |
| Serogroup C conjugate | 5 μg saccharide + 6.25-12.5 μg $CRM_{197}$ |
| Serogroup W135 conjugate | 5 μg saccharide + 3.3-10 μg $CRM_{197}$ |
| Serogroup Y conjugate | 5 μg saccharide + 3.3-10 μg $CRM_{197}$ |
| *Pneumococcus* serotype 4 conjugate | 2 μg saccharide + 2.5 μg $CRM_{197}$ |
| *Pneumococcus* serotype 9V conjugate | 2 μg saccharide + 2.5 μg $CRM_{197}$ |
| *Pneumococcus* serotype 14 conjugate | 2 μg saccharide + 2.5 μg $CRM_{197}$ |
| *Pneumococcus* serotype 18C conjugate | 2 μg saccharide + 2.5 μg $CRM_{197}$ |
| *Pneumococcus* serotype 19F conjugate | 2 μg saccharide + 2.5 μg $CRM_{197}$ |
| *Pneumococcus* serotype 23F conjugate | 2 μg saccharide + 2.5 μg $CRM_{197}$ |
| *Pneumococcus* serotype 6B conjugate | 4 μg saccharide + 5 μg $CRM_{197}$ |

It will be understood that the invention has been described by way of example only and modifications may be made whilst remaining within the scope and spirit of the invention.

TABLE 1

| | 2996 | NGH38 | M4215 | MC58 | 44/76 | CU385 | N44/89 | 394/98 | M01-240149 | NM092 |
|---|---|---|---|---|---|---|---|---|---|---|
| Typing: | B:2b:P1.5a, 2a | B:NT:P1.3 | B:15:P1.7, 16 | B:15:P1.7, 16b | B:15:P1.7, 16 | B:4:P1.15 | B:4, 7:P1.19, 15 | B:4:P1.4 | B:4:P1.7, 4 | B:4:P1.4 |
| ET: | other | other | n.d. | ET5 | ET5 | ET5 | ET5 | lin. 3 | lin. 3 | lin 3 |
| Positive control | 32768 | 32768 | 32768 | 16384 | 16384 | >16384 | 8192 | 16384 | 8192 | 32768 |
| Antigen mixture | 4096 | 4096 | 65536 | 32768 | 65536 | >65536 | >4096 | 8192 | 2048 | >4096 |
| Antigens + H44/76 OMVs | 16384 | 8192 | >65536 | 32768 | 524288 | >65536 | >4096 | 16384 | 8192 | >4096 |
| Antigens + 394/98 OMV | 8192 | 8192 | >65536 | 32768 | >65536 | >65536 | >4096 | 65536 | >8192 | >4096 |
| OMVs (Norway) | <4 | 1024 | 8192 | 2048 | 262144 | 256 | <8 | 4096 | <4 | <8 |
| OMVs (NZ) | 512 | <4 | 128 | 2048 | <4 | <8 | <8 | 32768 | >8192 | 4096 |

| | | NM008 | BZ198 | 961-5945 | G2136 | 5/99 | F6124 | BZ133 | LPN17592 | 240539 |
|---|---|---|---|---|---|---|---|---|---|---|
| | Typing: | B:4:P1.4 | B:NT | B:2b:P1.21, 16 | B: | B:2b:P1.5, 2 | A | C:NT: | W135 | P1.5 |
| | ET: | lin 3 | lin 3 | A4 | A4 | A4 | sIII | sI | | |
| | Positive control | 8192 | 16384 | 8192 | 32768 | 8192 | 1024 | | 1024 | 4096 |
| | Antigen mixture | 4096 | 4096 | 2048 | 2048 | >4096 | 8192 | 16384 | 4096 | >8192 |

TABLE 1-continued

| | | | | | | | | | |
|---|---|---|---|---|---|---|---|---|---|
| Antigens + H44/76 OMVs | >4096 | >4096 | >8192 | 2048 | >4096 | 32768 | 32768 | 16384 | >8192 |
| Antigens + 394/98 OMV | >4096 | >4096 | 2048 | 8192 | >4096 | 65536 | 65536 | 65536 | >8192 |
| OMVs (Norway) | <8 | <4 | >8192 | <8 | <8 | 1024 | <4 | <8 | >4096 |
| OMVs (NZ) | 1024 | 4096 | <16 | n.d. | <8 | 4096 | 1024 | <8 | >4096 |

REFERENCES

The Contents of which are Hereby Incorporated by Reference

[1] Maiden et al. (1998) *PNAS USA* 95:3140-3145.
[2] Armand et al. (1982) *J. Biol. Stand.* 10:335-339.
[3] Cadoz et al. (1985) *Vaccine* 3:340-342.
[4] Bjune et al. (1991) *Lancet* 338(8775):1093-96
[5] Parkhill et al. (2000) *Nature* 404:502-506.
[6] Tettelin et al. (2000) *Science* 287:1809-1815.
[7] WO00/66791.
[8] WO99/24578.
[9] WO99/36544.
[10] WO99/57280.
[11] WO00/22430.
[12] WO00/66741.
[13] Pizza et al. (2000) *Science* 287:1816-1820.
[14] WO01/64920.
[15] WO01/64922.
[16] WO03/020756.
[17] Comanducci et al. (2002) *J. Exp. Med.* 195:1445-1454.
[18] WO03/010194.
[19] UK patent application 0227346.4.
[20] WO03/063766.
[21] Masignani et al. (2003) *J Exp Med* 197:789-799.
[22] http://neisseria.org/nm/typing/mlst/
[23] Pettersson et al. (1994) *Microb Pathog* 17(6):395-408.
[24] Welsch et al. (2002) Thirteenth International Pathogenic Neisseria Conference, Norwegian Institute of Public Health, Oslo, Norway; Sep. 1-6, 2002. *Genome-derived antigen (GNA) 2132 elicits protective serum antibodies to groups B and C Neisseria meningitidis strains.*
[25] Santos et al. (2002) Thirteenth International Pathogenic Neisseria Conference, Norwegian Institute of Public Health, Oslo, Norway; Sep. 1-6, 2002. *Serum bactericidal responses in rhesus macaques immunized with novel vaccines containing recombinant proteins derived from the genome of N. meningitidis.*
[26] WO03/009869.
[27] WO01/30390.
[28] Almeida & Alpar (1996) *J. Drug Targeting* 3:455-467.
[29] Agarwal & Mishra (1999) *Indian J Exp Biol* 37:6-16.
[30] WO00/53221.
[31] Jakobsen et al. (2002) *Infect Immun* 70:1443-1452.
[32] Wu et al. (1997) *J Infect Dis* 175:839-846.
[33] Bergquist et al. (1998) *APMIS* 106:800-806.
[34] Baudner et al. (2002) *Infect Immun* 70:4785-4790.
[35] Ugozzoli et al. (2002) *J Infect Dis* 186:1358-1361.
[36] Paoletti et al. (2001) *Vaccine* 19:2118-2126.
[37] WO00/56365.
[38] Gennaro (2000) *Remington: The Science and Practice of Pharmacy.* 20th edition, ISBN: 0683306472.
[39] *Vaccine Design . . .* (1995) eds. Powell & Newman. ISBN: 030644867X. Plenum.
[40] WO00/23105.
[41] WO90/14837.
[42] U.S. Pat. No. 5,057,540.
[43] WO96/33739.
[44] EP-A-0109942.
[45] WO96/11711.
[46] WO00/07621.
[47] Barr et al. (1998) *Advanced Drug Delivery Reviews* 32:247-271.
[48] Sjolanderet et al. (1998) *Advanced Drug Delivery Reviews* 32:321-338.
[49] Niikura et al. (2002) *Virology* 293:273-280.
[50] Lenz et al. (2001) *J Immunol* 166:5346-5355.
[51] Pinto et al. (2003) *J Infect Dis* 188:327-338.
[52] Gerber et al. (2001) *Virol* 75:47524760.
[53] WO03/024480
[54] WO03/024481
[55] Gluck et al. (2002) *Vaccine* 20:B10-B16.
[56] EP-A-0689454.
[57] Johnson et al. (1999) *Bioorg Med Chem Lett* 9:2273-2278.
[58] Evans et al. (2003) *Expert Rev Vaccines* 2:219-229.
[59] Meraldi et al. (2003) *Vaccine* 21:2485-2491.
[60] Pajak et al. (2003) *Vaccine* 21:836-842.
[61] Kandimalla et al. (2003) *Nucleic Acids Research* 31:2393-2400.
[62] WO02/26757.
[63] WO99/62923.
[64] Krieg (2003) *Nature Medicine* 9:831-835.
[65] McCluskie et al. (2002) *FEMS Immunology and Medical Microbiology* 32:179-185.
[66] WO98/40100.
[67] U.S. Pat. No. 6,207,646.
[68] U.S. Pat. No. 6,239,116.
[69] U.S. Pat. No. 6,429,199.
[70] Kandimalla et al. (2003) *Biochemical Society Transactions* 31 (part 3):654-658.
[71] Blackwell et al. (2003) *J Immunol* 170:4061-4068.
[72] Krieg (2002) *Trends Immunol* 23:64-65.
[73] WO01/95935.
[74] Kandimalla et al. (2003) *BBRC* 306:948-953.
[75] Bhagat et al. (2003) *BBRC* 300:853-861.
[76] WO03/035836.
[77] WO95/17211.
[78] WO98/42375.
[79] Beignon et al. (2002) *Infect Immun* 70:3012-3019.
[80] Pizza et al. (2001) *Vaccine* 19:2534-2541.
[81] Pizza et al. (2000) *Int J Med Microbiol* 290:455-461.
[82] Scharton-Kersten et al. (2000) *Infect Immun* 68:5306-5313.
[83] Ryan et al. (1999) *Infect Immun* 67:6270-6280.
[84] Partidos et al. (1999) *Immunol Lett* 67:209-216.
[85] Peppoloni et al. (2003) *Expert Rev Vaccines* 2:285-293.
[86] Pine et al. (2002) *J Control Release* 85:263-270.
[87] Domenighini et al. (1995) *Mol Microbiol* 15:1165-1167.

[88] WO99/40936.
[89] WO99/44636.
[90] Singh et al] (2001) *J Cont Release* 70:267-276.
[91] WO99/27960.
[92] U.S. Pat. No. 6,090,406
[93] U.S. Pat. No. 5,916,588
[94] EP-A-0626169.
[95] WO99/52549.
[96] WO01/21207.
[97] WO01/21152.
[98] Andrianov et al. (1998) *Biomaterials* 19:109-115.
[99] Payne et al. (1998) *Adv Drug Delivery Review* 31:185-196.
[100] Stanley (2002) *Clin Exp Dermatol* 27:571-577.
[101] Jones (2003) *Curr Opin Investig Drugs* 4:214-218.
[102] WO99/11241.
[103] WO94/00153.
[104] WO98/57659.
[105] European patent applications 0835318, 0735898 and 0761231.
[106] WO96/37222; U.S. Pat. No. 6,333,036.
[107] Costantino et al. (1992) *Vaccine* 10:691-698.
[108] WO03/007985.
[109] Bell (2000) *Pediatr Infect Dis J* 19:1187-1188.
[110] Iwarson (1995) *APMIS* 103:321-326.
[111] Gerlich et al. (1990) *Vaccine* 8 Suppl:S63-68 & 79-80.
[112] *Vaccines* (1988) eds. Plotkin & Mortimer. ISBN 0-7216-1946-0.
[113] Del Guidice et al. (1998) *Molecular Aspects of Medicine* 19:1-70.
[114] Gustafsson et al. (1996) *N. Engl. J. Med.* 334:349-355.
[115] Rappuoli et al. (1991) *TIBTECH* 9:232-238.
[116] WO01/52885.
[117] Fukasawa et al. (1999) *Vaccine* 17:2951-2958.
[118] Rosenqvist et al. (1998) *Dev. Biol. Stand.* 92:323-333.
[119] Sutter et al. (2000) *Pediatr Clin North Am* 47:287-308.
[120] Zimmerman & Spann (1999) *Am Fam Physician* 59:113-118, 125-126.
[121] Robinson & Torres (1997) *Seminars in Immunology* 9:271-283.
[122] Donnelly et al. (1997) *Annu Rev Immunol* 15:617-648.
[123] Scott-Taylor & Dalgleish (2000) *Expert Opin Investig Drugs* 9:471-480.
[124] Apostolopoulos & Plebanski (2000) *Curr Opin Mol Ther* 2:441-447.
[125] Ilan (1999) *Curr Opin Mol Ther* 1:116-120.
[126] Dubensky et al. (2000) *Mol Med* 6:723-732.
[127] Robinson & Pertmer (2000) *Adv Virus Res* 55:1-74.
[128] Donnelly et al. (2000) *Am J Respir Crit Care Med* 162(4 Pt 2):S190-193.
[129] Davis (1999) *Mt. Sinai J. Med* 66:84-90.
[130] Charalambous & Feavers (2001) *J Med Microbiol* 50:937-939.
[131] Westerink (2001) *Int Rev Immunol* 20:251-261.
[132] Grothaus et al. (2000) *Vaccine* 18:1253-1263.
[133] Jones (2001) *Curr Opin Investig Drugs* 2:47-49.
[134] Ravenscroft et al. (1999) *Vaccine* 17:2802-2816.
[135] Costantino et al. (1999) *Vaccine* 17:1251-1263.
[136] WO03/080678.
[137] Nilsson & Svensson (1979) *Carbohydrate Research* 69: 292-296)
[138] Frash (1990) p. 123-145 of *Advances in Biotechnological Processes* vol. 13 (eds. Mizrahi & Van Wezel)
[139] Inzana (1987) *Infect. Immun.* 55:1573-1579.
[140] Kandil et al. (1997) *Glycoconj J* 14:13-17.
[141] Berkin et al. (2002) *Chemistry* 8:4424-4433.
[142] Lindberg (1999) *Vaccine* 17 Suppl 2:S28-36.
[143] Buttery & Moxon (2000) *JR Coll Physicians Lond* 34:163-168.
[144] Ahmad & Chapnick (1999) *Infect Dis Clin North Am* 13:113-33, vii.
[145] Goldblatt (1998) *J. Med. Microbiol.* 47:563-567.
[146] European patent 0477508.
[147] U.S. Pat. No. 5,306,492.
[148] WO98/42721.
[149] Dick et al. in *Conjugate Vaccines* (eds. Cruse et al.) Karger, Basel, 1989, 10:48-114.
[150] Hermanson *Bioconjugate Techniques*, Academic Press, San Diego (1996) ISBN: 0123423368.
[151] Kanra et al. (1999) *The Turkish Journal of Paediatrics* 42:421-427.
[152] Ravenscroft et al. (2000) *Dev Biol (Basel)* 103: 35-47.
[153] WO97/00697.
[154] WO02/00249.
[155] Watson (2000) *Pediatr Infect Dis J* 19:331-332.
[156] Rubin (2000) *Pediatr Clin North Am* 47:269-285, v.
[157] Jedrzejas (2001) *Microbiol Mol Biol Rev* 65:187-207.
[158] Zielen et al. (2000) *Infect. Immun.* 68:1435-1440.
[159] Darkes & Plosker (2002) *Paediatr Drugs* 4:609-630.
[160] Tettelin et al. (2001) *Science* 293:498-506.
[161] Hoskins et al. (2001) *J Bacteriol* 183:5709-5717.
[162] Rappuoli (2000) *Curr Opin Microbiol* 3:445-450
[163] Rappuoli (2001) *Vaccine* 19:2688-2691.
[164] Masignani et al. (2002) *Expert Opin Biol Ther* 2:895-905.
[165] Mora et al. (2003) *Drug Discov Today* 8:459-464.
[166] Wizemann et al. (2001) *Infect Immun* 69:1593-1598.
[167] Rigden et al. (2003) *Crit Rev Biochem Mol Biol* 38:143-168.
[168] WO02/22167.
[169] Ramsay et al. (2001) *Lancet* 357(9251):195-196.
[170] Anonymous (January 2002) *Research Disclosure*, 453077.
[171] Anderson (1983) *Infect Immun* 39(1):233-238.
[172] Anderson et al. (1985) *J Clin Invest* 76(1):52-59.
[173] EP-A-0372501.
[174] EP-A-0378881.
[175] EP-A-0427347.
[176] WO93/17712
[177] WO94/03208.
[178] WO98/58668.
[179] EP-A-0471177.
[180] WO91/01146
[181] Falugi et al. (2001) *Eur J Immunol* 31:3816-3824.
[182] EP-A-0594610.
[183] WO00/56360.
[184] WO02/091998.
[185] WO01/72337
[186] WO00/61761.
[187] WO99/42130
[188] WO96/40242
[189] Lees et al. (1996) *Vaccine* 14:190-198.
[190] WO95/08348.
[191] U.S. Pat. No. 4,882,317
[192] U.S. Pat. No. 4,695,624
[193] Porro et al. (1985) *Mol Immunol* 22:907-919.s
[194] EP-A-0208375
[195] WO00/10599
[196] Gever et al. Med. Microbiol. Immunol, 165: 171-288 (1979).
[197] U.S. Pat. No. 4,057,685.
[198] U.S. Pat. Nos. 4,673,574; 4,761,283; 4,808,700.
[199] U.S. Pat. No. 4,459,286.
[200] U.S. Pat. No. 4,965,338

[201] U.S. Pat. No. 4,663,160.
[202] U.S. Pat. No. 4,761,283
[203] U.S. Pat. No. 4,356,170
[204] Lei et al. (2000) *Dev Biol (Basel)* 103:259-264.
[205] WO00/38711; U.S. Pat. No. 6,146,902.
[206] *Current Protocols in Molecular Biology* (F. M. Ausubel et al., eds., 1987) Supplement 30.
[207] Smith & Waterman (1981) *Adv. Appl. Math.* 2: 482-489.

---

The invention claimed is:

1. An immunogenic composition comprising at least the following three Neisserial antigens: NadA, 287, and 741, wherein each of the three Neisserial antigens is purified and wherein said immunogenic composition also comprises an outer-membrane vesicle (OMV) preparation from *N. meningitidis*.

2. The immunogenic composition of claim 1, wherein the outer-membrane vesicle is obtained from *N. meningitidis* strain H44/76 or 394/98.

3. The immunogenic composition of claim 1, wherein the outer-membrane vesicle is obtained from *N. meningitidis* strain H44/76.

4. The immunogenic composition of any one of claims 1-3, further comprising an antigen from *N. meningitidis*.

5. The immunogenic composition of any one of claims 1-3, wherein all of the Neisserial antigens are *N. meningitidis* antigens.

6. The immunogenic composition of any one of claims 1-3, further comprising one or more saccharide antigens from *N. meningitidis*.

7. The immunogenic composition of claim 6, wherein the one or more saccharides antigens are from *N. meningitidis* serogroup A, C, W135 and/or Y.

8. The immunogenic composition of any one of claims 1-3, further comprising an adjuvant.

9. The immunogenic composition of claim 8, wherein the adjuvant is aluminum salt.

10. The immunogenic composition of claim 8, wherein the adjuvant is aluminum hydroxide gel.

* * * * *

UNITED STATES PATENT AND TRADEMARK OFFICE
CERTIFICATE OF CORRECTION

| | | |
|---|---|---|
| PATENT NO. | : 8,663,656 B2 | Page 1 of 1 |
| APPLICATION NO. | : 10/530753 | |
| DATED | : March 4, 2014 | |
| INVENTOR(S) | : Mariagrazia Pizza | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 663 days.

Signed and Sealed this
Twenty-fifth Day of August, 2015

Michelle K. Lee
*Director of the United States Patent and Trademark Office*

SEQUENCE LISTING

<160> NUMBER OF SEQ ID NOS: 12

<210> SEQ ID NO 1
<211> LENGTH: 350
<212> TYPE: PRT
<213> ORGANISM: N. meningitidis

<400> SEQUENCE: 1

```
Met Lys His Phe Pro Ser Lys Val Leu Thr Thr Ala Ile Leu Ala Thr
 1               5                  10                  15

Phe Cys Ser Gly Ala Leu Ala Ala Thr Asn Asp Asp Val Lys Lys
                20                  25                  30

Ala Ala Thr Val Ala Ile Ala Ala Tyr Asn Asn Gly Gln Glu Ile
                35                  40                  45

Asn Gly Phe Lys Ala Gly Glu Thr Ile Tyr Asp Ile Asp Glu Asp Gly
 50                  55                  60

Thr Ile Thr Lys Lys Asp Ala Thr Ala Asp Val Glu Ala Asp Asp
 65                  70                  75                  80

Phe Lys Gly Leu Gly Leu Lys Lys Val Val Thr Asn Leu Thr Lys Thr
                    85                  90                  95

Val Asn Glu Asn Lys Gln Asn Val Asp Ala Lys Val Lys Ala Ala Glu
                100                 105                 110

Ser Glu Ile Glu Lys Leu Thr Thr Lys Leu Ala Asp Thr Asp Ala Ala
                115                 120                 125

Leu Ala Asp Thr Asp Ala Ala Leu Asp Ala Thr Thr Asn Ala Leu Asn
            130                 135                 140

Lys Leu Gly Glu Asn Ile Thr Thr Phe Ala Glu Glu Thr Lys Thr Asn
145                 150                 155                 160

Ile Val Lys Ile Asp Glu Lys Leu Glu Ala Val Ala Asp Thr Val Asp
                    165                 170                 175

Lys His Ala Glu Ala Phe Asn Asp Ile Ala Asp Ser Leu Asp Glu Thr
                180                 185                 190

Asn Thr Lys Ala Asp Glu Ala Val Lys Thr Ala Asn Glu Ala Lys Gln
                195                 200                 205

Thr Ala Glu Glu Thr Lys Gln Asn Val Asp Ala Lys Val Lys Ala Ala
            210                 215                 220

Glu Thr Ala Ala Gly Lys Ala Glu Ala Ala Gly Thr Ala Asn Thr
225                 230                 235                 240

Ala Ala Asp Lys Ala Glu Ala Val Ala Lys Val Thr Asp Ile Lys
                245                 250                 255

Ala Asp Ile Ala Thr Asn Lys Ala Asn Ile Ala Lys Lys Ala Asn Ser
                    260                 265                 270

Ala Asp Val Tyr Thr Arg Glu Glu Ser Asp Ser Lys Phe Val Arg Ile
                275                 280                 285

Asp Gly Leu Asn Ala Thr Thr Glu Lys Leu Asp Thr Arg Leu Ala Ser
            290                 295                 300

Ala Glu Lys Ser Ile Ala Asp His Asp Thr Arg Leu Asn Gly Leu Asp
305                 310                 315                 320

Lys Thr Val Ser Asp Leu Arg Lys Glu Thr Arg Gln Gly Leu Ala Glu
                    325                 330                 335
```

```
Gln Ala Ala Leu Ser Gly Leu Phe Gln Pro Tyr Asn Val Gly
        340                 345                 350

<210> SEQ ID NO 2
<211> LENGTH: 327
<212> TYPE: PRT
<213> ORGANISM: N. meningitidis

<400> SEQUENCE: 2

Ala Thr Asn Asp Asp Val Lys Lys Ala Thr Val Ala Ile Ala
 1               5                  10                  15

Ala Ala Tyr Asn Asn Gly Gln Glu Ile Asn Gly Phe Lys Ala Gly Glu
                20                  25                  30

Thr Ile Tyr Asp Ile Asp Glu Asp Gly Thr Ile Thr Lys Lys Asp Ala
            35                  40                  45

Thr Ala Ala Asp Val Glu Ala Asp Asp Phe Lys Gly Leu Gly Leu Lys
        50                  55                  60

Lys Val Val Thr Asn Leu Thr Lys Thr Val Asn Glu Asn Lys Gln Asn
 65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
            100                 105                 110

Leu Asp Ala Thr Thr Asn Ala Leu Asn Lys Leu Gly Glu Asn Ile Thr
        115                 120                 125

Thr Phe Ala Glu Glu Thr Lys Thr Asn Ile Val Lys Ile Asp Glu Lys
130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
        195                 200                 205

Glu Ala Ala Ala Gly Thr Ala Asn Thr Ala Ala Asp Lys Ala Glu Ala
    210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
                245                 250                 255

Glu Ser Asp Ser Lys Phe Val Arg Ile Asp Gly Leu Asn Ala Thr Thr
            260                 265                 270

Glu Lys Leu Asp Thr Arg Leu Ala Ser Ala Glu Lys Ser Ile Ala Asp
        275                 280                 285

His Asp Thr Arg Leu Asn Gly Leu Asp Lys Thr Val Ser Asp Leu Arg
    290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
                325

<210> SEQ ID NO 3
<211> LENGTH: 248
<212> TYPE: PRT
<213> ORGANISM: N. meningitidis
```

```
<400> SEQUENCE: 3

Val Ala Asp Ile Gly Ala Gly Leu Ala Asp Ala Leu Thr Ala Pro
 1               5                  10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
 50                      55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
            115                 120                 125

Gly Glu His Thr Ser Phe Asp Lys Leu Pro Glu Gly Gly Arg Ala Thr
130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
            180                 185                 190

Pro Asp Gly Lys Arg His Ala Val Ile Ser Gly Ser Val Leu Tyr Asn
            195                 200                 205

Gln Ala Glu Lys Gly Ser Tyr Ser Leu Gly Ile Phe Gly Gly Lys Ala
            210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 4
<211> LENGTH: 179
<212> TYPE: PRT
<213> ORGANISM: N. meningitidis

<400> SEQUENCE: 4

Val Ser Ala Val Ile Gly Ser Ala Ala Val Gly Ala Lys Ser Ala Val
 1               5                  10                  15

Asp Arg Arg Thr Thr Gly Ala Gln Thr Asp Asp Asn Val Met Ala Leu
            20                  25                  30

Arg Ile Glu Thr Thr Ala Arg Ser Tyr Leu Arg Gln Asn Asn Gln Thr
            35                  40                  45

Lys Gly Tyr Thr Pro Gln Ile Ser Val Val Gly Tyr Asn Arg His Leu
 50                      55                  60

Leu Leu Leu Gly Gln Val Ala Thr Glu Gly Glu Lys Gln Phe Val Gly
 65                  70                  75                  80

Gln Ile Ala Arg Ser Glu Gln Ala Ala Glu Gly Val Tyr Asn Tyr Ile
                85                  90                  95

Thr Val Ala Ser Leu Pro Arg Thr Ala Gly Asp Ile Ala Gly Asp Thr
            100                 105                 110
```

```
Trp Asn Thr Ser Lys Val Arg Ala Thr Leu Leu Gly Ile Ser Pro Ala
        115                 120                 125

Thr Gln Ala Arg Val Lys Ile Val Thr Tyr Gly Asn Val Thr Tyr Val
130                 135                 140

Met Gly Ile Leu Thr Pro Glu Glu Gln Ala Gln Ile Thr Gln Lys Val
145                 150                 155                 160

Ser Thr Thr Val Gly Val Gln Lys Val Ile Thr Leu Tyr Gln Asn Tyr
                165                 170                 175

Val Gln Arg

<210> SEQ ID NO 5
<211> LENGTH: 168
<212> TYPE: PRT
<213> ORGANISM: N. meningitidis

<400> SEQUENCE: 5

Ala Thr Tyr Lys Val Asp Glu Tyr His Ala Asn Ala Arg Phe Ala Ile
1               5                   10                  15

Asp His Phe Asn Thr Ser Thr Asn Val Gly Gly Phe Tyr Gly Leu Thr
                20                  25                  30

Gly Ser Val Glu Phe Asp Gln Ala Lys Arg Asp Gly Lys Ile Asp Ile
            35                  40                  45

Thr Ile Pro Ile Ala Asn Leu Gln Ser Gly Ser Gln His Phe Thr Asp
    50                  55                  60

His Leu Lys Ser Ala Asp Ile Phe Asp Ala Ala Gln Tyr Pro Asp Ile
65                  70                  75                  80

Arg Phe Val Ser Thr Lys Phe Asn Phe Asn Gly Lys Lys Leu Val Ser
                85                  90                  95

Val Asp Gly Asn Leu Thr Met His Gly Lys Thr Ala Pro Val Lys Leu
            100                 105                 110

Lys Ala Glu Lys Phe Asn Cys Tyr Gln Ser Pro Met Glu Lys Thr Glu
        115                 120                 125

Val Cys Gly Gly Asp Phe Ser Thr Thr Ile Asp Arg Thr Lys Trp Gly
130                 135                 140

Met Asp Tyr Leu Val Asn Val Gly Met Thr Lys Ser Val Arg Ile Asp
145                 150                 155                 160

Ile Gln Ile Glu Ala Ala Lys Gln
                165

<210> SEQ ID NO 6
<211> LENGTH: 464
<212> TYPE: PRT
<213> ORGANISM: N. meningitidis

<400> SEQUENCE: 6

Ser Pro Asp Val Lys Ser Ala Asp Thr Leu Ser Lys Pro Ala Ala Pro
1               5                   10                  15

Val Val Ser Glu Lys Glu Thr Glu Ala Lys Glu Asp Ala Pro Gln Ala
                20                  25                  30

Gly Ser Gln Gly Gln Gly Ala Pro Ser Ala Gln Gly Ser Gln Asp Met
            35                  40                  45

Ala Ala Val Ser Glu Glu Asn Thr Gly Asn Gly Gly Ala Val Thr Ala
    50                  55                  60

Asp Asn Pro Lys Asn Glu Asp Glu Val Ala Gln Asn Asp Met Pro Gln
65                  70                  75                  80

Asn Ala Ala Gly Thr Asp Ser Ser Thr Pro Asn His Thr Pro Asp Pro
                85                  90                  95
```

```
Asn Met Leu Ala Gly Asn Met Glu Asn Gln Ala Thr Asp Ala Gly Glu
            100                 105                 110

Ser Ser Gln Pro Ala Asn Gln Pro Asp Met Ala Asn Ala Ala Asp Gly
            115                 120                 125

Met Gln Gly Asp Asp Pro Ser Ala Gly Gln Asn Ala Gly Asn Thr
130                 135                 140

Ala Ala Gln Gly Ala Asn Gln Ala Gly Asn Asn Gln Ala Ala Gly Ser
145                 150                 155                 160

Ser Asp Pro Ile Pro Ala Ser Asn Pro Ala Pro Ala Asn Gly Gly Ser
            165                 170                 175

Asn Phe Gly Arg Val Asp Leu Ala Asn Gly Val Leu Ile Asp Gly Pro
            180                 185                 190

Ser Gln Asn Ile Thr Leu Thr His Cys Lys Gly Asp Ser Cys Ser Gly
            195                 200                 205

Asn Asn Phe Leu Asp Glu Glu Val Gln Leu Lys Ser Glu Phe Glu Lys
            210                 215                 220

Leu Ser Asp Ala Asp Lys Ile Ser Asn Tyr Lys Lys Asp Gly Lys Asn
225                 230                 235                 240

Asp Lys Phe Val Gly Leu Val Ala Asp Ser Val Gln Met Lys Gly Ile
            245                 250                 255

Asn Gln Tyr Ile Ile Phe Tyr Lys Pro Lys Pro Thr Ser Phe Ala Arg
            260                 265                 270

Phe Arg Arg Ser Ala Arg Ser Arg Arg Ser Leu Pro Ala Glu Met Pro
            275                 280                 285

Leu Ile Pro Val Asn Gln Ala Asp Thr Leu Ile Val Asp Gly Glu Ala
            290                 295                 300

Val Ser Leu Thr Gly His Ser Gly Asn Ile Phe Ala Pro Glu Gly Asn
305                 310                 315                 320

Tyr Arg Tyr Leu Thr Tyr Gly Ala Glu Lys Leu Pro Gly Gly Ser Tyr
            325                 330                 335

Ala Leu Arg Val Gln Gly Glu Pro Ala Lys Gly Glu Met Leu Ala Gly
            340                 345                 350

Ala Ala Val Tyr Asn Gly Glu Val Leu His Phe His Thr Glu Asn Gly
            355                 360                 365

Arg Pro Tyr Pro Thr Arg Gly Arg Phe Ala Ala Lys Val Asp Phe Gly
            370                 375                 380

Ser Lys Ser Val Asp Gly Ile Ile Asp Ser Gly Asp Asp Leu His Met
385                 390                 395                 400

Gly Thr Gln Lys Phe Lys Ala Ala Ile Asp Gly Asn Gly Phe Lys Gly
            405                 410                 415

Thr Trp Thr Glu Asn Gly Ser Gly Asp Val Ser Gly Lys Phe Tyr Gly
            420                 425                 430

Pro Ala Gly Glu Glu Val Ala Gly Lys Tyr Ser Tyr Arg Pro Thr Asp
            435                 440                 445

Ala Glu Lys Gly Gly Phe Gly Val Phe Ala Gly Lys Lys Glu Gln Asp
    450                 455                 460

<210> SEQ ID NO 7
<211> LENGTH: 644
<212> TYPE: PRT
<213> ORGANISM: N. meningitidis

<400> SEQUENCE: 7

Met Ala Ser Pro Asp Val Lys Ser Ala Asp Thr Leu Ser Lys Pro Ala
1               5                   10                  15
```

-continued

```
Ala Pro Val Val Ser Glu Lys Glu Thr Glu Ala Lys Glu Asp Ala Pro
         20                  25                  30
Gln Ala Gly Ser Gln Gly Gln Gly Ala Pro Ser Ala Gln Gly Gly Gln
         35                  40                  45
Asp Met Ala Ala Val Ser Glu Glu Asn Thr Gly Asn Gly Gly Ala Ala
 50                  55                  60
Ala Thr Asp Lys Pro Lys Asn Glu Asp Glu Gly Ala Gln Asn Asp Met
 65                  70                  75                  80
Pro Gln Asn Ala Ala Asp Thr Asp Ser Leu Thr Pro Asn His Thr Pro
                 85                  90                  95
Ala Ser Asn Met Pro Ala Gly Asn Met Glu Asn Gln Ala Pro Asp Ala
                100                 105                 110
Gly Glu Ser Glu Gln Pro Ala Asn Gln Pro Asp Met Ala Asn Thr Ala
                115                 120                 125
Asp Gly Met Gln Gly Asp Asp Pro Ser Ala Gly Glu Asn Ala Gly
130                 135                 140
Asn Thr Ala Ala Gln Gly Thr Asn Gln Ala Glu Asn Asn Gln Thr Ala
145                 150                 155                 160
Gly Ser Gln Asn Pro Ala Ser Ser Thr Asn Pro Ser Ala Thr Asn Ser
                165                 170                 175
Gly Gly Asp Phe Gly Arg Thr Asn Val Gly Asn Ser Val Val Ile Asp
                180                 185                 190
Gly Pro Ser Gln Asn Ile Thr Leu Thr His Cys Lys Gly Asp Ser Cys
                195                 200                 205
Ser Gly Asn Asn Phe Leu Asp Glu Glu Val Gln Leu Lys Ser Glu Phe
210                 215                 220
Glu Lys Leu Ser Asp Ala Asp Lys Ile Ser Asn Tyr Lys Lys Asp Gly
225                 230                 235                 240
Lys Asn Asp Gly Lys Asn Asp Lys Phe Val Gly Leu Val Ala Asp Ser
                245                 250                 255
Val Gln Met Lys Gly Ile Asn Gln Tyr Ile Ile Phe Tyr Lys Pro Lys
                260                 265                 270
Pro Thr Ser Phe Ala Arg Phe Arg Ser Ala Arg Ser Arg Arg Ser
                275                 280                 285
Leu Pro Ala Glu Met Pro Leu Ile Pro Val Asn Gln Ala Asp Thr Leu
290                 295                 300
Ile Val Asp Gly Glu Ala Val Ser Leu Thr Gly His Ser Gly Asn Ile
305                 310                 315                 320
Phe Ala Pro Glu Gly Asn Tyr Arg Tyr Leu Thr Tyr Gly Ala Glu Lys
                325                 330                 335
Leu Pro Gly Gly Ser Tyr Ala Leu Arg Val Gln Gly Glu Pro Ser Lys
                340                 345                 350
Gly Glu Met Leu Ala Gly Thr Ala Val Tyr Asn Gly Glu Val Leu His
                355                 360                 365
Phe His Thr Glu Asn Gly Arg Pro Ser Pro Ser Arg Gly Arg Phe Ala
370                 375                 380
Ala Lys Val Asp Phe Gly Ser Lys Ser Val Asp Gly Ile Ile Asp Ser
385                 390                 395                 400
Gly Asp Gly Leu His Met Gly Thr Gln Lys Phe Lys Ala Ala Ile Asp
                405                 410                 415
Gly Asn Gly Phe Lys Gly Thr Trp Thr Glu Asn Gly Gly Asp Val
                420                 425                 430
Ser Gly Lys Phe Tyr Gly Pro Ala Gly Glu Glu Val Ala Gly Lys Tyr
```

```
                    435                 440                 445
Ser Tyr Arg Pro Thr Asp Ala Glu Lys Gly Gly Phe Gly Val Phe Ala
450                 455                 460
Gly Lys Lys Glu Gln Asp Gly Ser Gly Gly Gly Ala Thr Tyr Lys
465                 470                 475                 480
Val Asp Glu Tyr His Ala Asn Ala Arg Phe Ala Ile Asp His Phe Asn
                485                 490                 495
Thr Ser Thr Asn Val Gly Gly Phe Tyr Gly Leu Thr Gly Ser Val Glu
            500                 505                 510
Phe Asp Gln Ala Lys Arg Asp Gly Lys Ile Asp Ile Thr Ile Pro Val
        515                 520                 525
Ala Asn Leu Gln Ser Gly Ser Gln His Phe Thr Asp His Leu Lys Ser
530                 535                 540
Ala Asp Ile Phe Asp Ala Ala Gln Tyr Pro Asp Ile Arg Phe Val Ser
545                 550                 555                 560
Thr Lys Phe Asn Phe Asn Gly Lys Lys Leu Val Ser Val Asp Gly Asn
                565                 570                 575
Leu Thr Met His Gly Lys Thr Ala Pro Val Lys Leu Lys Ala Glu Lys
            580                 585                 590
Phe Asn Cys Tyr Gln Ser Pro Met Ala Lys Thr Glu Val Cys Gly Gly
        595                 600                 605
Asp Phe Ser Thr Thr Ile Asp Arg Thr Lys Trp Gly Val Asp Tyr Leu
610                 615                 620
Val Asn Val Gly Met Thr Lys Ser Val Arg Ile Asp Ile Gln Ile Glu
625                 630                 635                 640
Ala Ala Lys Gln

<210> SEQ ID NO 8
<211> LENGTH: 434
<212> TYPE: PRT
<213> ORGANISM: N. meningitidis

<400> SEQUENCE: 8

Met Val Ser Ala Val Ile Gly Ser Ala Ala Val Gly Ala Lys Ser Ala
  1               5                  10                  15
Val Asp Arg Arg Thr Thr Gly Ala Gln Thr Asp Asp Asn Val Met Ala
                 20                  25                  30
Leu Arg Ile Glu Thr Thr Ala Arg Ser Tyr Leu Arg Gln Asn Asn Gln
             35                  40                  45
Thr Lys Gly Tyr Thr Pro Gln Ile Ser Val Val Gly Tyr Asn Arg His
         50                  55                  60
Leu Leu Leu Leu Gly Gln Val Ala Thr Glu Gly Glu Lys Gln Phe Val
 65                  70                  75                  80
Gly Gln Ile Ala Arg Ser Glu Gln Ala Ala Glu Gly Val Tyr Asn Tyr
                 85                  90                  95
Ile Thr Val Ala Ser Leu Pro Arg Thr Ala Gly Asp Ile Ala Gly Asp
                100                 105                 110
Thr Trp Asn Thr Ser Lys Val Arg Ala Thr Leu Leu Gly Ile Ser Pro
            115                 120                 125
Ala Thr Gln Ala Arg Val Lys Ile Val Thr Tyr Gly Asn Val Thr Tyr
        130                 135                 140
Val Met Gly Ile Leu Thr Pro Glu Glu Gln Ala Gln Ile Thr Gln Lys
145                 150                 155                 160
Val Ser Thr Thr Val Gly Val Gln Lys Val Ile Thr Leu Tyr Gln Asn
                165                 170                 175
```

Tyr Val Gln Arg Gly Ser Gly Gly Gly Val Ala Ala Asp Ile Gly
                180                 185                 190

Ala Gly Leu Ala Asp Ala Leu Thr Ala Pro Leu Asp His Lys Asp Lys
            195                 200                 205

Gly Leu Gln Ser Leu Thr Leu Asp Gln Ser Val Arg Lys Asn Glu Lys
210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
            260                 265                 270

Gly Glu Phe Gln Val Tyr Lys Gln Ser His Ser Ala Leu Thr Ala Phe
        275                 280                 285

Gln Thr Glu Gln Ile Gln Asp Ser Glu His Ser Gly Lys Met Val Ala
    290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr Arg Gly Thr Ala Phe
                325                 330                 335

Gly Ser Asp Asp Ala Gly Gly Lys Leu Thr Tyr Thr Ile Asp Phe Ala
            340                 345                 350

Ala Lys Gln Gly Asn Gly Lys Ile Glu His Leu Lys Ser Pro Glu Leu
        355                 360                 365

Asn Val Asp Leu Ala Ala Ala Asp Ile Lys Pro Asp Gly Lys Arg His
    370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
                405                 410                 415

Ala Glu Val Lys Thr Val Asn Gly Ile Arg His Ile Gly Leu Ala Ala
            420                 425                 430

Lys Gln

<210> SEQ ID NO 9
<211> LENGTH: 6
<212> TYPE: PRT
<213> ORGANISM: Unknown
<220> FEATURE:
<223> OTHER INFORMATION: Linker

<400> SEQUENCE: 9

Gly Ser Gly Gly Gly Gly
 1               5

<210> SEQ ID NO 10
<211> LENGTH: 255
<212> TYPE: PRT
<213> ORGANISM: N. meningitidis

<400> SEQUENCE: 10

Cys Ser Ser Gly Gly Gly Gly Val Ala Ala Asp Ile Gly Ala Gly Leu
 1               5                  10                  15

Ala Asp Ala Leu Thr Ala Pro Leu Asp His Lys Asp Lys Gly Leu Gln
            20                  25                  30

```
Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                    85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                    165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                    245                 250                 255

<210> SEQ ID NO 11
<211> LENGTH: 254
<212> TYPE: PRT
<213> ORGANISM: N. meningitidis

<400> SEQUENCE: 11

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                    85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
130                 135                 140
```

```
Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250
```

<210> SEQ ID NO 12
<211> LENGTH: 262
<212> TYPE: PRT
<213> ORGANISM: N. meningitidis

<400> SEQUENCE: 12

```
Cys Ser Ser Gly Gly Gly Ser Gly Gly Gly Gly Val Ala Ala Asp
1               5                   10                  15

Ile Gly Thr Gly Leu Ala Asp Ala Leu Thr Ala Pro Leu Asp His Lys
                20                  25                  30

Asp Lys Gly Leu Lys Ser Leu Thr Leu Glu Asp Ser Ile Pro Gln Asn
            35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asn His Ser
                100                 105                 110

Ala Val Val Ala Leu Gln Ile Glu Lys Ile Asn Asn Pro Asp Lys Thr
            115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Arg Ile Glu His Leu Lys
            180                 185                 190

Thr Leu Glu Gln Asn Val Glu Leu Ala Ala Ala Glu Leu Lys Ala Asp
    195                 200                 205

Glu Lys Ser His Ala Val Ile Leu Gly Asp Thr Arg Tyr Gly Ser Glu
210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
                260
```